(12) United States Patent
McGinley et al.

(10) Patent No.: US 9,492,181 B2
(45) Date of Patent: Nov. 15, 2016

(54) DRILL WITH DEPTH MEASUREMENT SYSTEM AND LIGHT EMITTER

(71) Applicant: McGinley Engineered Solutions, LLC, Casper, WY (US)

(72) Inventors: Joseph C. McGinley, Casper, WY (US); Kevin D. Simmons, San Francisco, CA (US); Peter A. Privitera, San Francisco, CA (US); Henry K. Sim, Mountain View, CA (US); Shigeru Tanaka, Half Moon Bay, CA (US); David J. Rinaldis, Redwood City, CA (US); Graham R. Faulknor, San Mateo, CA (US); Martin A. Leugers, San Francisco, CA (US)

(73) Assignee: McGinley Engineered Solutions, LLC, Casper, WY (US)

( * ) Notice: Subject to any disclaimer, the term of this patent is extended or adjusted under 35 U.S.C. 154(b) by 0 days.

(21) Appl. No.: 14/047,705

(22) Filed: Oct. 7, 2013

(65) Prior Publication Data

US 2015/0066030 A1    Mar. 5, 2015

Related U.S. Application Data

(63) Continuation of application No. 14/018,252, filed on Sep. 4, 2013, now Pat. No. 9,370,372.

(51) Int. Cl.
*A61B 17/16* (2006.01)
*A61B 17/14* (2006.01)

(52) U.S. Cl.
CPC ............ *A61B 17/16* (2013.01); *A61B 17/1615* (2013.01); *A61B 17/1622* (2013.01); *A61B 17/1626* (2013.01); *A61B 17/148* (2013.01);

(Continued)

(58) Field of Classification Search
CPC .............. A61B 17/16; A61B 17/1613; A61B 17/1615; A61B 17/1617; A61B 17/162; A61B 17/1622; A61B 17/1624; A61B 17/1626; A61B 17/1628
See application file for complete search history.

(56) References Cited

U.S. PATENT DOCUMENTS

| 1,831,813 | A | * | 11/1931 | Levedahl | ................. 408/81 |
| 2,883,891 | A | * | 4/1959 | Robinson et al. | ............ 408/112 |
| 3,804,544 | A | | 4/1974 | Adams | |

(Continued)

FOREIGN PATENT DOCUMENTS

WO    2015034562    3/2015

OTHER PUBLICATIONS

PCT/US2014/038974 Search Report and Written Opinion from the international Searching Authority, Oct. 12, 2014, 18 pages.

*Primary Examiner* — Christian Sevilla
*Assistant Examiner* — Eric S Gibson
(74) *Attorney, Agent, or Firm* — Marsh Fischmann & Breyfogle LLP

(57) ABSTRACT

A measurement system and method for determining a depth of penetration of a working portion of a surgical instrument (e.g., a rotating drill bit in a bore). A first sensor outputs a first signal representative of a displacement of the leading edge of the drill bit in the bore. A second sensor outputs a second signal representative of a force applied to the leading edge of the drill bit. A processor outputs a third signal representative of the depth of penetration of the leading edge of the drill bit when the leading edge of the drill bit passes from a first medium having a first density to a second medium having a second density. The third signal is based on the first and second signals.

7 Claims, 25 Drawing Sheets

(52) U.S. Cl.
CPC ........ *A61B 17/162* (2013.01); *A61B 2090/062* (2016.02)

(56) References Cited

U.S. PATENT DOCUMENTS

| | | | |
|---|---|---|---|
| 4,014,621 A | 3/1977 | Johnson et al. | |
| 4,157,231 A * | 6/1979 | Phillips | 408/1 R |
| 4,310,269 A * | 1/1982 | Neu et al. | 408/11 |
| 4,329,092 A * | 5/1982 | Ponitzsch et al. | 408/11 |
| 4,329,095 A * | 5/1982 | Schmuck | 408/112 |
| 4,644,335 A * | 2/1987 | Wen | 340/683 |
| 4,710,075 A | 12/1987 | Davison | |
| 4,723,911 A | 2/1988 | Kurtz | |
| 4,765,333 A | 8/1988 | Bray | |
| 4,867,158 A | 9/1989 | Sugg | |
| 4,951,690 A | 8/1990 | Baker | |
| 5,014,793 A * | 5/1991 | Germanton et al. | 173/181 |
| 5,022,798 A | 6/1991 | Eckman | |
| 5,071,293 A * | 12/1991 | Wells | 408/112 |
| 5,139,376 A | 8/1992 | Pumphrey | |
| 5,161,921 A | 11/1992 | Corsi | |
| 5,277,799 A | 1/1994 | Bransch | |
| 5,361,504 A | 11/1994 | Huang | |
| 5,380,333 A | 1/1995 | Meloul et al. | |
| 5,411,503 A * | 5/1995 | Hollstien et al. | 606/86 R |
| 5,533,842 A * | 7/1996 | Johnson et al. | 408/17 |
| 5,538,423 A * | 7/1996 | Coss et al. | 433/27 |
| 5,584,838 A * | 12/1996 | Rona et al. | 606/96 |
| 5,599,142 A * | 2/1997 | Fujimoto et al. | 408/10 |
| 5,613,810 A * | 3/1997 | Bureller | 408/3 |
| 5,810,828 A | 9/1998 | Lightman et al. | 606/80 |
| 5,961,257 A * | 10/1999 | Bettini et al. | 408/97 |
| 5,980,248 A * | 11/1999 | Kusakabe et al. | 433/27 |
| 6,033,409 A * | 3/2000 | Allotta | 606/80 |
| 6,081,741 A | 6/2000 | Hollis | |
| 6,096,042 A * | 8/2000 | Herbert | 606/80 |
| 6,342,057 B1 | 1/2002 | Brace et al. | |
| 6,494,590 B1 * | 12/2002 | Paganini | B25F 5/021 362/109 |
| 6,527,778 B2 * | 3/2003 | Athanasiou et al. | 606/80 |
| 6,587,184 B2 | 7/2003 | Würsch et al. | |
| 6,665,948 B1 * | 12/2003 | Kozin et al. | 33/833 |
| 6,786,683 B2 * | 9/2004 | Schaer et al. | 408/16 |
| 6,925,725 B2 * | 8/2005 | Herrmann et al. | 33/638 |
| 7,073,989 B2 * | 7/2006 | Erickson et al. | 408/97 |
| 7,185,998 B2 * | 3/2007 | Oomori | B25B 23/18 362/119 |
| 7,220,088 B2 | 5/2007 | Ferrari et al. | |
| 7,235,940 B2 * | 6/2007 | Bosch et al. | 318/432 |
| 7,482,819 B2 | 1/2009 | Wuersch | |
| 7,578,642 B2 * | 8/2009 | Fritsche et al. | 408/76 |
| 7,681,659 B2 * | 3/2010 | Zhang et al. | 173/1 |
| 7,946,049 B1 * | 5/2011 | Wilton | 33/526 |
| 7,992,311 B2 * | 8/2011 | Cerwin | B23B 49/006 33/286 |
| 8,167,518 B2 * | 5/2012 | Mathis et al. | 408/1 R |
| 8,317,437 B2 * | 11/2012 | Merkley et al. | 408/9 |
| 8,460,297 B2 | 6/2013 | Watlington et al. | |
| 8,734,153 B2 * | 5/2014 | Arzanpour et al. | 433/114 |
| 8,925,169 B2 * | 1/2015 | Schevers | 29/407.08 |
| 9,114,494 B1 * | 8/2015 | Mah | B23Q 17/2233 |
| 2001/0047219 A1 | 11/2001 | Oden | 700/159 |
| 2003/0049082 A1 * | 3/2003 | Morrison et al. | 408/56 |
| 2004/0146367 A1 | 7/2004 | Gerhardt et al. | 408/110 |
| 2004/0179829 A1 | 9/2004 | Phillips et al. | 388/804 |
| 2004/0215395 A1 | 10/2004 | Strasser et al. | 702/9 |
| 2005/0116673 A1 | 6/2005 | Carl et al. | 318/432 |
| 2005/0131415 A1 * | 6/2005 | Hearn et al. | 606/80 |
| 2005/0169717 A1 * | 8/2005 | Field | 408/13 |
| 2005/0261870 A1 * | 11/2005 | Cramer | B23B 49/008 702/166 |
| 2006/0004371 A1 | 1/2006 | Williams et al. | |
| 2006/0008771 A1 * | 1/2006 | Courvoisier | 433/165 |
| 2007/0030486 A1 * | 2/2007 | Gelbart | B23Q 17/2233 356/399 |
| 2007/0035311 A1 * | 2/2007 | Wuersch | 324/644 |
| 2007/0041799 A1 | 2/2007 | Schaefer et al. | |
| 2008/0167653 A1 | 7/2008 | Watlington et al. | |
| 2008/0292416 A1 | 11/2008 | Kado et al. | |
| 2009/0131986 A1 | 5/2009 | Lee et al. | |
| 2009/0245956 A1 * | 10/2009 | Apkarian et al. | 408/1 R |
| 2009/0299439 A1 * | 12/2009 | Mire et al. | 607/60 |
| 2009/0326537 A1 * | 12/2009 | Anderson | 606/80 |
| 2010/0114099 A1 | 5/2010 | Patwardhan | |
| 2010/0137874 A1 * | 6/2010 | Kim et al. | 606/102 |
| 2010/0239380 A1 | 9/2010 | Amirov et al. | |
| 2011/0060242 A1 * | 3/2011 | Hausman | A61B 17/1626 600/554 |
| 2011/0245831 A1 | 10/2011 | Giersch et al. | |
| 2011/0245832 A1 | 10/2011 | Giersch et al. | |
| 2011/0245833 A1 * | 10/2011 | Anderson | 606/80 |
| 2011/0301611 A1 * | 12/2011 | Garcia et al. | 606/80 |
| 2012/0037386 A1 * | 2/2012 | Cook | B23B 45/001 173/30 |
| 2012/0253348 A1 | 10/2012 | Arlettaz et al. | |
| 2013/0304069 A1 * | 11/2013 | Bono et al. | 606/80 |
| 2013/0307529 A1 * | 11/2013 | Baumgartner | 324/207.2 |
| 2014/0107471 A1 * | 4/2014 | Haider | A61B 17/14 600/424 |
| 2015/0066038 A1 * | 3/2015 | McGinley et al. | 606/80 |
| 2015/0165580 A1 * | 6/2015 | Holland | B23Q 17/2275 408/1 BD |

\* cited by examiner

BICORTICAL DRILL PATH

UNICORTICAL DRILL PATH

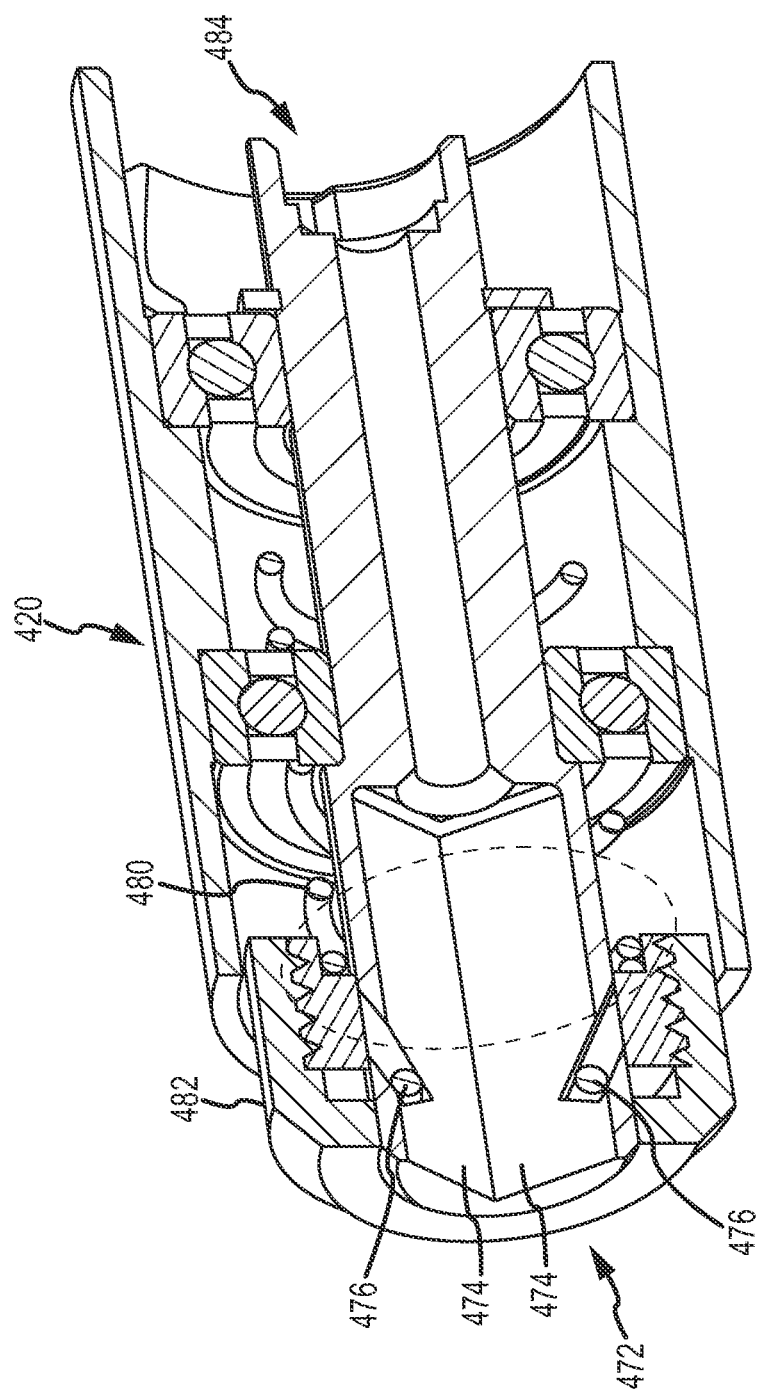

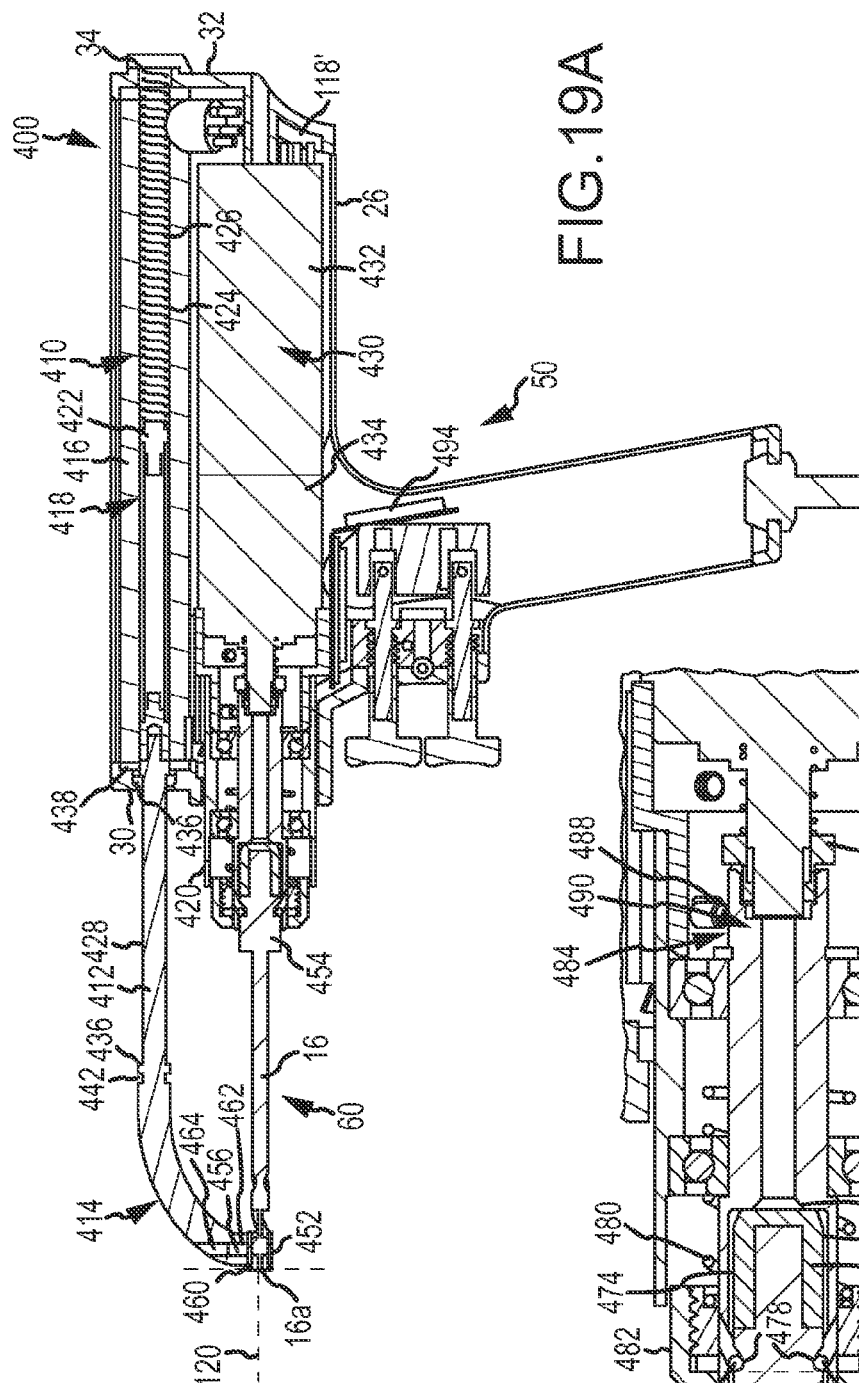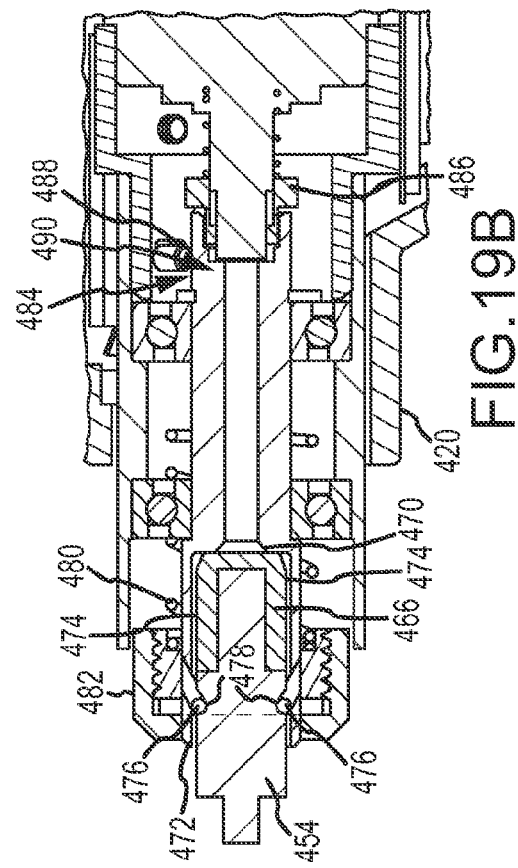

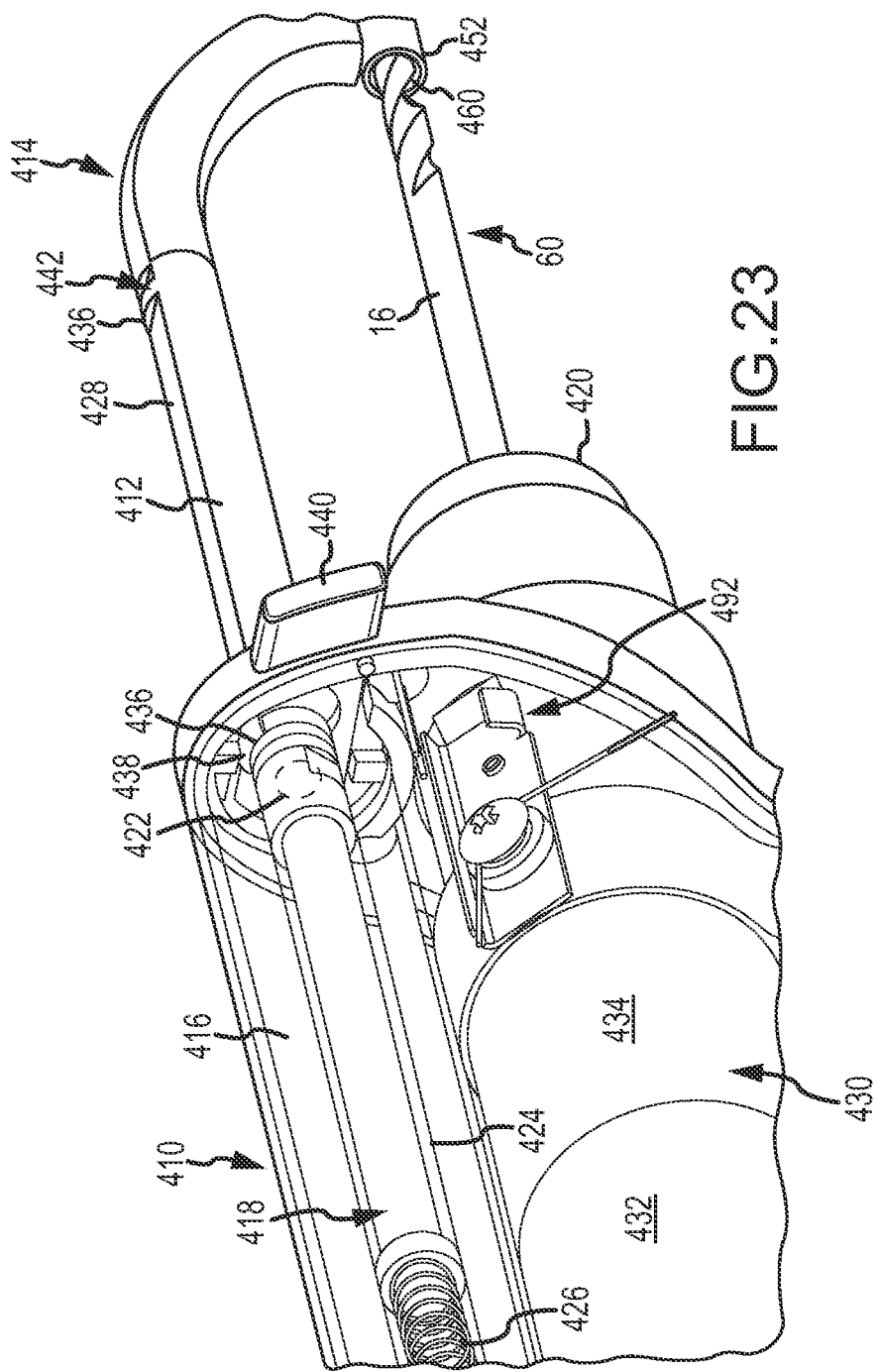

DRILL WITH DEPTH MEASUREMENT SYSTEM AND LIGHT EMITTER

CROSS REFERENCE TO RELATED APPLICATIONS

This application is a continuation of U.S. application Ser. No. 14/018,252 filed on Sep. 4, 2013 entitled "DRILL BIT PENETRATION MEASUREMENT SYSTEMS AND METHODS", the entirety of which is incorporated by reference herein.

BACKGROUND

Inadequate and inaccurate depth measurement following orthopedic drilling procedures may result in incorrect screw lengths, which can lead to surgical complications. Furthermore, determining the correct screw length for a bore can be a time consuming procedure which is undesirable when tissue is exposed and potentially subjected to infection.

As shown in FIGS. 1A and 1B, the bony structure of the human anatomy consists mainly of cortical bone 10 having a hard outer cortex 12 and a soft inner medullary layer 14. Following traumatic injury, plate and screw placement is critical for adequate repair of a fractured bone. Improper drilling lengths could lead to device instability, damage to anatomic structures, or device failure.

As shown in FIG. 1A, when using a rotating drill bit 16 to form a bicortical bore 18 through the cortical bone 10, the rotating drill bit 16 passes through a first portion 12a of the hard outer cortex 12, a soft non-resistant medullary layer 14, and a second portion 12b of the hard outer cortex 12.

As shown in FIG. 1B, when using a rotating drill bit 16 to form a unicortical bore 20 through the cortical bone 10, the rotating drill bit 16 passes through an entry point 22a of the hard outer cortex 12 and an exit point 22b of the hard outer cortex 12 without penetrating the soft non-resistant medullary layer 14.

Previously proposed techniques for drilling and screw placement have been two-step processes, at best. For example, during an operation, a bore is first drilled by a surgeon until the surgeon "feels" the drill bit pass completely through the bony structure. That is, the surgeon must rely on his or her senses alone to determine when the drill bit has passed completely through the bony structure. Once the surgeon believes that he or she has passed completely through the structure, the drill bit is removed from the bore and a depth gage (not shown) is then inserted into the bore. The depth gage is grasped against the proximal end and a depth is recorded. A possible resulting complication of this procedure is that the surgeon may not precisely "feel" the drill bit pass through the second cortical layer, thereby possibly damaging tissue on the opposite side of the bone. Another complication may occur if the depth gage is not properly inserted into the hole. If the gage is grasped prior to passing the distal end of the bore, a size will be determined that is smaller than the true depth.

The process of drilling and depth measurement often requires more than one attempt. Conservative drilling may result in incomplete drilling requiring multiple passes. Furthermore, multiple depth measurements may be required to confirm accurate placement of the gage. This process consumes a substantial amount of surgical time resulting in a large cost per patient. By combining the drilling and depth measurement process into one accurate procedure, cost is reduced along with a decrease in patient morbidity.

SUMMARY

The present disclosure relates generally to systems, methods, and apparatuses for use in connection with determining, with respect to a reference point, a depth of penetration of an instrument working portion (e.g., a leading edge of a rotating drill bit in a bore) when the instrument working portion (e.g., a leading edge of the drill bit) is advanced (e.g., in the bore). More specifically, the present invention relates to a system and method for determining the length of either a unicortical or bicortical bore made in a bone of a patient without removing the drill bit from the bore formed in the bone. Accordingly, the present disclosure may find application in the field of surgical drilling where the length of the bore made through a bone is to be determined to, for example, determine the appropriate size of hardware to be used in connection with the bore that has been drilled.

Specifically, the present disclosure is related to embodiments of drill bit assemblies, drills, and/or drilling systems that may be specifically adapted for use for drill bit penetration measurement. Accordingly, the drill bit assemblies and drills disclosed herein may provide increased efficiency, reliability, and accuracy in relation to a drill bit penetration measurement system. For instance, in certain embodiments, a drill bit assembly may be used in conjunction with a drill as described herein to provide an improved platform to facilitate measurement of a bore created by the drill using a drill bit penetration measurement system without having to remove the drill bit from the bore during operation. However, it may be appreciated that the measurement systems described herein may be utilized with other surgical instruments such as, for example, a surgical saw, a surgical grinder, of a surgical chisel to determine a depth of penetration of a working portion of the instrument relative to a reference point.

In this regard, systems for drill bit penetration measurement systems have been proposed such as described in U.S. Pat. No. 6,665,948, the entirety of which is incorporated herein by reference. In this regard, the description presented herein may provide refinements and/or additional features for use in connection with a drill bit penetration measurement system. As such, the efficiency, accuracy, and or ergonomics of drill bit penetration measurement systems may be improved.

Accordingly, a first aspect includes a drill bit assembly for use with a drill having a displacement sensor for outputting a signal representative of a displacement of the drill bit with respect to a reference point. The assembly includes a drill bit, a bushing, and an engagement member disposed on the bushing. The drill bit has a leading edge disposed at a distal end of the drill bit and a shank disposed adjacent to a proximal end of the drill bit. The drill bit includes a cylindrical member extending between the distal end and the shank. The shank is adapted for engagement with a chuck of a drill, and the cylindrical member extends along an axis of rotation about which the cylindrical member rotates during drilling. The bushing includes an aperture sized to receive at least a portion of the cylindrical member through the aperture. As such, the bushing is constrainedly moveable relative to the cylindrical member in a direction along the axis of rotation. The engagement member is adapted for engagement with a displacement sensing arm of the displacement sensor. In this regard, the engagement member is engageable with the displacement sensing arm for corresponding movement between the bushing and the displacement sensing arm.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For example, in an embodiment, the aperture of the bushing may define a cylindrical opening extending from a distal end of the bushing to a proximal end of the bushing. In this case, the distal end of the cylindrical opening may comprise a reference surface. The reference surface may extend at least partially circumferentially about the drill bit. In other embodiments, the bushing may be conformably shaped relative to the cylindrical member to facilitate the constrained movement relative to the axis of rotation. In such embodiments, the bushing may or may not extend about entirety of the circumference of the cylindrical member. For example, the bushing may include a dished or concave surface that is alignable with the cylindrical member for constrained movement in a direction along the drilling axis.

In any regard, the bushing may be disposable adjacent the distal end of the bit. Accordingly, the reference surface may be alignable with the leading edge of the drill bit to define a reference point from which displacement of the drill bit may be measured. In this regard, the displacement sensing arm to which the bushing is engageable may be operatively engaged with a displacement sensor of a drill as will be described in greater detail below. In this regard, the drill bit is rotatably advanceable into a bore such that the leading edge of the drill bit is displaced relative to the reference surface upon the rotatable advancement of the drill bit into the bore. Accordingly, when the engagement member operatively engages a displacement sensing arm of a displacement sensor, the displacement sensor may measure the displacement of the leading edge from the reference surface.

In an embodiment, the reference surface may contact a peripheral portion extending about the bore upon rotational advancement of the drill bit to create the bore. The bushing may be maintainably engagable against the peripheral portion extending about the bore so as to maintain the reference point stationary against the peripheral portion of the bore in a direction along the axis of rotation. For instance, the bushing may be biased toward the distal end of the drill bit (e.g., under the influence of the displacement sensing arm or by another biasing member disposed relative to the drill bit and bushing). In this regard, as the reference surface of the bushing may be maintained adjacent to the surface to be drilled, the accuracy of the displacement measure upon rotational advancement of the drill bit may be improved given the proximity of contact of the bushing defining the reference surface relative to the location of the bore.

In various embodiments, the engagement member may comprise any appropriate mechanism for attachably connecting the bushing to a displacement sensing arm. In one particular embodiment, the engagement member may include a post extending from the bushing that is selectively engageable with the displacement sensing arm of the displacement sensor. In this regard, the post may facilitate relative rotational movement about an axis of the post between the bushing and the displacement sensing arm (e.g., prior to engagement of the shank with a chuck of the drill). This rotational movement may allow for improved ergonomics when engaging the drill bit assembly with a drill by allowing the shank to be aligned with a chuck of a drill after engagement of the post with the displacement sensing arm.

In an embodiment, the drill bit assembly may be provided as a one-time use, disposable component for use in a surgery or other operation. In this regard, the drill bit assembly may include features that help reduce the likelihood that the drill bit is reused in contradiction of instructions regarding one time use. Such features may at least reduce the functionality of the drill bit assembly (e.g., potentially to the point where the drill bit assembly is incapable of reuse). For example, in an embodiment, the shank may include a destructible portion that is at least partially destructible during a cleaning process. In one particular embodiment, the destructible portion may be meltable. In this regard, a melting temperature of the destructible portion may be greater than an operating temperature of the drill bit and less than an autoclave temperature. As such, the destructible portion may remain intact during operation of the drill bit assembly. However, upon undergoing a cleaning or sterilization process (e.g., autoclaving), the destructible portion may be at least partially degraded. In one embodiment, the melting temperature of the destructible portion is not less than about 60° C. and not greater than about 110° C. The destructible portion may also be destroyed upon exposure to a cleaning or sanitizing chemical or the like used in the cleaning process (e.g., as an alternative to or in addition to being meltable).

In view of the foregoing, the destruction of the destructible portion may alter the shape of the shank of the drill bit such that engagement with a drill may be at least partially prevented or degraded. For instance, the destructible portion may be used to at least partially establish registration between the shank and a chuck to which the drill bit assembly is to be attached. Accordingly, upon destruction of the destructible portion, registration between the drill bit assembly and a chuck may be reduced (e.g., potentially to the point of inoperability of the drill bit). For example, the destructible portion may include a proximal end portion of the shank. In this regard, the destructible portion may include at least a portion of an engagement feature for engagement of the shank by a chuck. In an embodiment, the destructible portion may include at least a portion of at least one sidewall of the shank. Additionally or alternatively, the engagement feature may include a detent engageable by an engagement member in the chuck. As such, the destructible portion, after having been exposed to a cleaning process, may not be registerable with respect to the chuck. That is, the surface area of the engagement feature of the shank in contact with the chuck may be at least reduced upon exposure of the destructible portion to a cleaning process.

A second aspect includes a method for use of a drill bit assembly with a drill having a displacement sensor for outputting a signal representative of a displacement of a leading edge of the drill bit assembly with respect to a reference point. The method includes engaging a displacement sensing arm of the displacement sensor with an engagement member of a bushing. The bushing is constrainedly moveable relative to a drill bit along an axis of rotation about which the drill bit rotates during drilling. The engaging may result in corresponding movement of the bushing and the displacement sensing arm. The method may include aligning a shank of the drill bit with a chuck member of the drill and securing the shank of the drill bit with the chuck of the drill to restrict axial movement between the drill bit and the chuck.

A number of feature refinements and additional features are applicable to the second aspect. These feature refinements and additional features may be used individually or in any combination. As such, each of the following features that will be discussed may be, but are not required to be, used with any other feature or combination of features of the second aspect. For example, in an embodiment, the drill bit assembly may be provided in accord with any of the features and/or feature refinements described above in connection with the first aspect.

Additionally, in an embodiment, the method may include positioning a distal portion of the bushing adjacent to a leading edge of the drill bit at a distal portion thereof. In this regard, the method may also include contacting the leading edge of the drill bit to a surface of a medium to be drilled. Accordingly, the distal portion of the bushing may contact the surface of the medium to be drilled. As such, the method may also include establishing the reference point when the leading edge of the drill bit and the distal portion of the bushing are in contact with the surface of the medium to be drilled. The method may also include rotationally advancing the drill bit into the medium to be drilled, such that the leading edge advances in relation to the distal portion of the bushing in contact with the surface of the medium to be drilled. Thus, the method may include producing relative movement of the displacement sensing arm relative to the displacement sensor upon rotationally advancing the drill bit into the medium. As the displacement sensing arm may be operatively engaged with the displacement sensor, the method may further include outputting a signal from the displacement sensor indicative of the amount of displacement of the leading edge of the drill bit relative to the distal portion of the bushing.

A third aspect includes a drill bit for use in a medical drill for single use applications. The drill bit includes a leading edge, a shank, a cylindrical member, and a destructible portion. The leading edge is disposed at a distal end of the drill bit. The shank is disposed adjacent to a proximal end of the drill bit, and the cylindrical member extends along an axis of rotation between the distal end and the proximal end. The drill bit is rotatable about the axis of rotation during drilling. Additionally, the shank comprises the destructible portion that is at least partially destructible during a cleaning process.

A number of feature refinements and additional features are applicable to the third aspect. These feature refinements and additional features may be used individually or in any combination. As such, each of the following features that will be discussed may be, but are not required to be, used with any other feature or combination of features of the third aspect or any of the other aspects disclosed herein.

For example, in an embodiment, the destructible portion may be meltable. In this regard, a melting temperature of the destructible portion may be greater than an operating temperature of the drill bit and less than an autoclave temperature. For instance, the melting temperature of the destructible portion may be not less than about 60° C. and not greater than about 110° C. Additionally, as referenced above in connection with the first aspect, the destructible portion may be destroyed upon exposure to a cleaning or sanitizing chemical or the like used during a cleaning and/or sanitizing process.

As described above with respect to the first aspect, the destructible portion may comprise a proximal end portion of the shank. Thus, upon destruction of the destructible portion, at least a portion of the shank may undergo a change in shape. Accordingly, the destructible portion may include at least a portion of an engagement feature for engagement of the shank by a chuck. For instance, the destructible portion may include at least a portion of at least one sidewall of the shank. Additionally or alternatively, the engagement feature may include a detent engageable by the chuck (e.g., the detent features may correspond with a quick-change style chuck where the detents are used to selectively retain the shank in the chuck).

Accordingly, in an embodiment, the destructible portion, after having been exposed to a cleaning process, may not be registerable with respect to the chuck. In this regard, the surface area of the sidewall of the shank may be at least reduced upon exposure of the destructible portion to a cleaning process (e.g., an autoclave process or a chemical sanitation process).

A fourth aspect includes a method for a drill bit for use in a medical drill for single use applications. The method includes exposing the drill bit to a cleaning process and degrading at least a portion of a destructible portion disposed on a shank of the drill bit in response to the exposing. Additionally, a number of feature refinements and additional features are applicable to the fourth aspect. These feature refinements and additional features may be used individually or in any combination. As such, each of the following features that will be discussed may be, but are not required to be, used with any other feature or combination of features of any of the aspects discussed herein.

For instance, in an embodiment the exposing may include autoclaving the drill bit. As such, the degrading may include melting at least a portion of the destructible portion in response to the autoclaving. The melting may occur at a temperature of not less than about 60° C. and not greater than about 110° C. In this regard, the destructible portion may withstand temperatures associated with normal operation of the drill bit, but may be degraded (i.e., melted) upon exposure to the autoclaving process. In another embodiment, the exposing may include applying a cleaning chemical to the drill bit such that the degrading comprises removal of at least a portion of the destructible portion in response to applying the cleaning chemical.

In an embodiment, the degrading may result in changing a shape of a shank of the drill bit. Thus, the degrading may include removing at least a portion of the destructible portion at a shank of the drill bit. The portion of the destructible portion removed may at least be a portion of an engagement feature for engagement of the shank by a chuck. For instance, the destructible portion may include at least a portion of at least one sidewall of the shank or may include a detent engageable by the chuck. In any regard, the degrading may result in reducing the registration of the shank with respect to a chuck of a drill.

A fifth aspect includes a drill including a drill bit penetration measuring system for determining, with respect to a reference point, a depth of penetration of a leading edge of a drill bit in a bore. The drill includes a chuck for engagement with a shank of a drill bit. The chuck is operable to constrain a drill bit engaged by the chuck to limit relative axial movement relative to an axis of rotation about which the drill bit is rotated during drilling. The drill also includes a displacement sensing arm extending from the drill that is engageable with a bushing member that is constrainedly moveable with respect to (e.g., in a direction parallel to) the axis of rotation with respect to a drill bit engaged by the chuck. The drill also includes a displacement sensor disposed in a fixed relative position with respect to a drill bit engaged by the chuck at least in a direction corresponding to the axis of rotation. The displacement sensor is adapted for relative movement with respect to the displacement sensing arm. Accordingly, the displacement sensor is operative to output a first signal representative of the displacement of the drill sensing arm relative to the displacement sensor. The movement of the displacement sensing arm relative to the drill corresponds to displacement of the bushing relative to a drill bit engaged by the chuck. In this regard, movement of the displacement sensing arm relative to the drill and the corresponding movement of the drill bit relative to the bushing may be measured as an output of the displacement sensor of the drill.

A number of feature refinements and additional features are applicable to the fifth aspect. These feature refinements and additional features may be used individually or in any combination. As such, each of the following features that will be discussed may be, but are not required to be, used with any other feature or combination of features of the fifth aspect. Furthermore, any of the features discussed in relation to any other aspect discussed herein may be used with the fifth aspect.

For example, in an embodiment, the displacement sensor may be disposed internally to a drill housing and the displacement sensing arm may extend from the drill housing. Accordingly, the displacement sensing arm may extend from the drill housing parallel to and offset from the axis of rotation. As such, at least a portion of the displacement sensing arm (e.g., a distal portion thereof) may extend towards a drill bit engaged by the chuck. As such, the displacement sensing arm may include a hole engageable with a post of the bushing to effectuate corresponding movement of the displacement sensing arm and the bushing In an embodiment, the displacement sensor may include a linear variable differential displacement transducer (LVDT). Accordingly, a coil of the LVDT may be disposed in the housing and the displacement sensing arm may include a moveable core displaceable with respect to the coil of the LVDT. The displacement sensor may have a total measureable travel of at least about 2.5 inches (6.4 cm). Furthermore, the drill has a resolution of at least about 0.002 inches (0.06 mm). However, any other appropriate type of displacement sensor (e.g., a relative or absolute position sensor) may be used such as, for example, an optical sensor or the like.

In an embodiment, the displacement sensing arm may be biased to a distal position relative to a drill bit engaged by the chuck. Additionally or alternatively, the displacement sensing arm is selectively removable from the drill housing. Further still, the displacement sensing arm may be selectively retainable in a proximal position. The displacement sensing arm may be selectively removable from a passage extending through the drill housing, such that the passageway is selectively opened from a proximal end thereof to a distal end thereof (e.g., by removal of the displacement sensing arm and/or removal of an end cap or the like).

In an embodiment, the chuck of the drill may include a removable assembly engaged to a drive motor by way of a coupling receiver. The removable assembly may be attached to the drill by way of a release mechanism. As such, the chuck may be selectively removable from the drill.

In an embodiment, the drill may include a light emitter operable to emit light in a direction toward the drill bit retained by the chuck.

A sixth aspect includes a method for use of a drill including a drill bit penetration measuring system for determining, with respect to a reference point, a depth of penetration of leading edge of a drill bit in a bore. The method includes engaging a shank of a drill bit with a chuck of the drill. The method also includes constraining the drill bit engaged by the chuck to limit axial movement relative to an axis of rotation about which the drill bit is rotated during drilling. The method further includes connecting a displacement sensing arm extending from the drill to a bushing member that is constrainedly moveable along the axis of rotation with respect to the drill bit engaged with the chuck.

A number of feature refinements and additional features are applicable to the sixth aspect. These feature refinements and additional features may be used individually or in any combination. As such, each of the following features that will be discussed may be, but are not required to be, used with any other feature or combination of features of the sixth aspect. Furthermore, any of the features discussed in relation to any other aspect discussed herein may be used with the sixth aspect.

For example, the method may also include aligning a distal edge of the bushing with a leading edge of the drill bit and moving the displacement sensing arm relative to a displacement sensor of the drill. As such, the method may include establishing the reference point upon alignment of the distal edge of the bushing with the leading edge of the drill bit. Furthermore, the method may include rotating the drill bit to rotatably advance the drill bit in a bore and detecting a relative movement of the drill bit relative to the reference point by way of corresponding movement of the displacement sensing arm relative to the displacement sensor. Further still, the method may include biasing the displacement sensing arm to a distal position, wherein the biasing maintains the distal edge of the bushing in contact with a medium into which the drill bit is rotationally advanced.

A seventh aspect includes a drill comprising a drill bit penetration measurement system for determining, with respect to a reference point, a depth of a penetration of a leading edge of a rotating drill bit in a bore along an axis of rotation when the leading edge of the drill bit passes from a first medium to a second medium, the first medium contiguous with the second medium, the first medium having a first density, the second medium having a second density. The drill includes a first sensor outputting a first signal representative of a displacement, with respect to the reference point, of the leading edge of the drill bit in the bore and a second sensor outputting a second signal representative of a force applied to the leading edge of the drill bit. The drill also includes a chuck engageable with the drill bit. Accordingly, axial movement along the axis of rotation is constrained between the chuck and the drill bit. The drill also includes a motor that is operatively engaged with the chuck to rotate the drill bit. The motor is constrained rotationally about the axis of rotation by a suspension member. However, the suspension member allows for movement of the motor linearly along the axis of rotation relative to the second sensor. The drill also includes a processor in electrical communication with the first and second sensors. The processor is configured in a first mode to output a third signal representative of the depth of penetration of the leading edge of the drill bit when the leading edge of the drill bit passes from the first medium to the second medium. The third signal based on the first and second signals.

A number of feature refinements and additional features are applicable to the seventh aspect. These feature refinements and additional features may be used individually or in any combination. As such, each of the following features that will be discussed may be, but are not required to be, used with any other feature or combination of features of the seventh aspect. For example, any of the forgoing features described with respect to any other aspect disclosed herein may be utilized with the seventh aspect.

Additionally, in an embodiment the first sensor may be a linear variable differential displacement transducer (LVDT). In an embodiment, the second sensor may be a load cell. The third signal may be output when a second time derivative of the first signal is greater than zero and a first time derivative of the second signal is less than zero.

In an embodiment, the first sensor may be a linear variable differential displacement transducer (LVDT), the second signal may be a load cell, and the third signal may be output when the second time derivative of the first signal is greater than zero and a first time derivative of the second signal is less than zero. In an embodiment, the first medium may be cortical bone surrounded by the second medium and the first medium may enclose a third medium having a third density. In this regard, the system may include a mode selector and the processor may be configured to operate in a mode selected from the group of modes consisting of the first mode wherein the third signal corresponds to a length of a unicortical drill path and a second mode, wherein the processor is configured such that the third signal corresponds to a length of a bicortical drill path. In this regard, the first sensor may be a linear variable differential displacement transducer, the second sensor may be a load sensor, and the processor, in the first mode, outputs the third signal when a second time derivative of the first signal is greater than zero and a first time derivative of the second signal is less than zero. Also, the processor, in the second mode, may output the third signal in response to a second occurrence of the second time derivative of the first signal being greater than zero and the first time derivative of the second signal being less than zero.

In an embodiment, the third signal may include an alert perceivable by a user of the drill. The alert may be an auditory alert. Additionally or alternatively, the alert may include a change in speed of the motor of the drill. For example, the alert may include stopping the rotation of the motor of the drill.

A eighth aspect includes a surgical instrument that includes an instrument working portion adapted to engage a portion of a patient to perform a surgical operation. The surgical instrument also includes a light emitter adapted to emit light in a direction toward the patient when the instrument working portion is engaged with the portion of the patient to perform the surgical operation.

A number of feature refinements and additional features are applicable to the eighth aspect. These feature refinements and additional features may be used individually or in any combination. As such, each of the following features that will be discussed may be, but are not required to be, used with any other feature or combination of features of the eighth aspect. For example, any of the forgoing features described with respect to any or all of the foregoing aspects may be utilized with the eighth aspect.

For example, in an embodiment, the surgical instrument may correspond to any of the foregoing drill embodiments for determining a depth of penetration of a drill bit in a bore. However, in other embodiments, the surgical instrument may comprise a surgical saw, a surgical grinder, a surgical chisel, or some other surgical instrument without limitation.

In an embodiment, the light emitter may include a light emitting diode light source. For instance, in an embodiment, the light source may be disposed within a housing of the surgical instrument. Alternatively, the light source may be disposed remotely from the surgical instrument and transmitted to the light emitter (e.g., by way of fiber optics or the like).

In an embodiment, the surgical instrument may include a measurement system for determining, with respect to a reference point, a depth of the instrument working portion when the instrument working portion passes from a first medium to a second medium. As such, any of the foregoing discussion with respect to embodiments of measurement systems may be provided in various embodiments without limitation. For instance, the surgical instrument may include a first sensor outputting a first signal representative of a displacement, with respect to the reference point, of the instrument working portion, a second sensor outputting a second signal representative of a force applied to the instrument working portion, and a processor in electrical communication with the first and second sensors. The processor may be configured in a first mode to output a third signal representative of the depth of penetration of the instrument working portion of the surgical instrument when the instrument working portion passes from the first medium to the second medium, the third signal based on the first and second signals.

In an embodiment, the light emitter may be selectively operable between an emitting state and a non-emitting state. For instance, the emitting state may occur upon operation of the instrument working portion, and the non-emitting state may occur upon cessation of operation of the instrument working portion. Additionally or alternatively, the light emitter may be selectively changed between the emitting state and non-emitting state by way of a state switch or the like.

BRIEF DESCRIPTION OF THE FIGURES

FIG. 15 is a perspective view of an embodiment of a chuck for engagement of the bit of FIG. 13;

FIG. 16 is a perspective view in cross section of the embodiment of the chuck of FIG. 15;

FIGS. 19A and 19B are cross sectional views of an embodiment of a drill comprising a drill bit penetration measurement system;

FIG. 23 is a perspective view of an embodiment of a drill with a portion of the drill housing cut away to show the interaction of a displacement sensing arm with the drill housing and an embodiment of a chuck release.

DETAILED DESCRIPTION

Figure 1A:
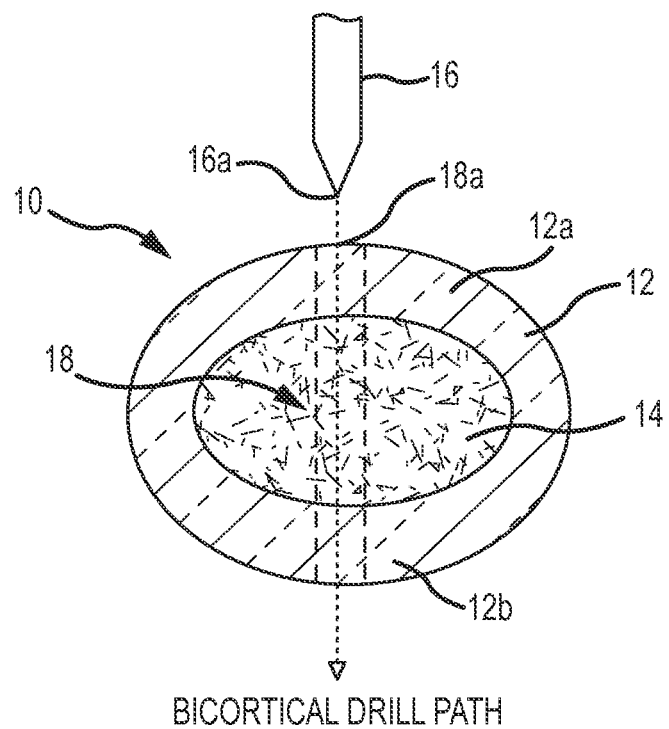
FIG. 1A is a sectional view of a bone illustrating a prior art method of using a drill mechanism to create a bicortical path through a cortical bone having multiple layers.

Certain terminology is used in the following description for convenience only and is not limiting. The words "right," "left", "lower" and "upper" designate directions in the drawings to which reference is made. The words "inwardly" and "outwardly" refer to directions toward and away from, respectively, the geometric center of the drill bit penetration measurement system and designated parts thereof. The terminology includes the words above specifically mentioned, derivatives thereof and words of similar import.

Additionally, as used in the claims and in the corresponding portion of the specification, the word "a" means "at least one". Further, unless otherwise defined the word "about" when used in conjunction with a numerical value means a range of values corresponding to the numerical value plus or minus ten percent of the numerical value. Still further, the word "or" has the meaning of a Boolean inclusive "Or". For example, the phrase "A or B" means "A" alone or "B" alone or both "A" and "B".

Figure 10:
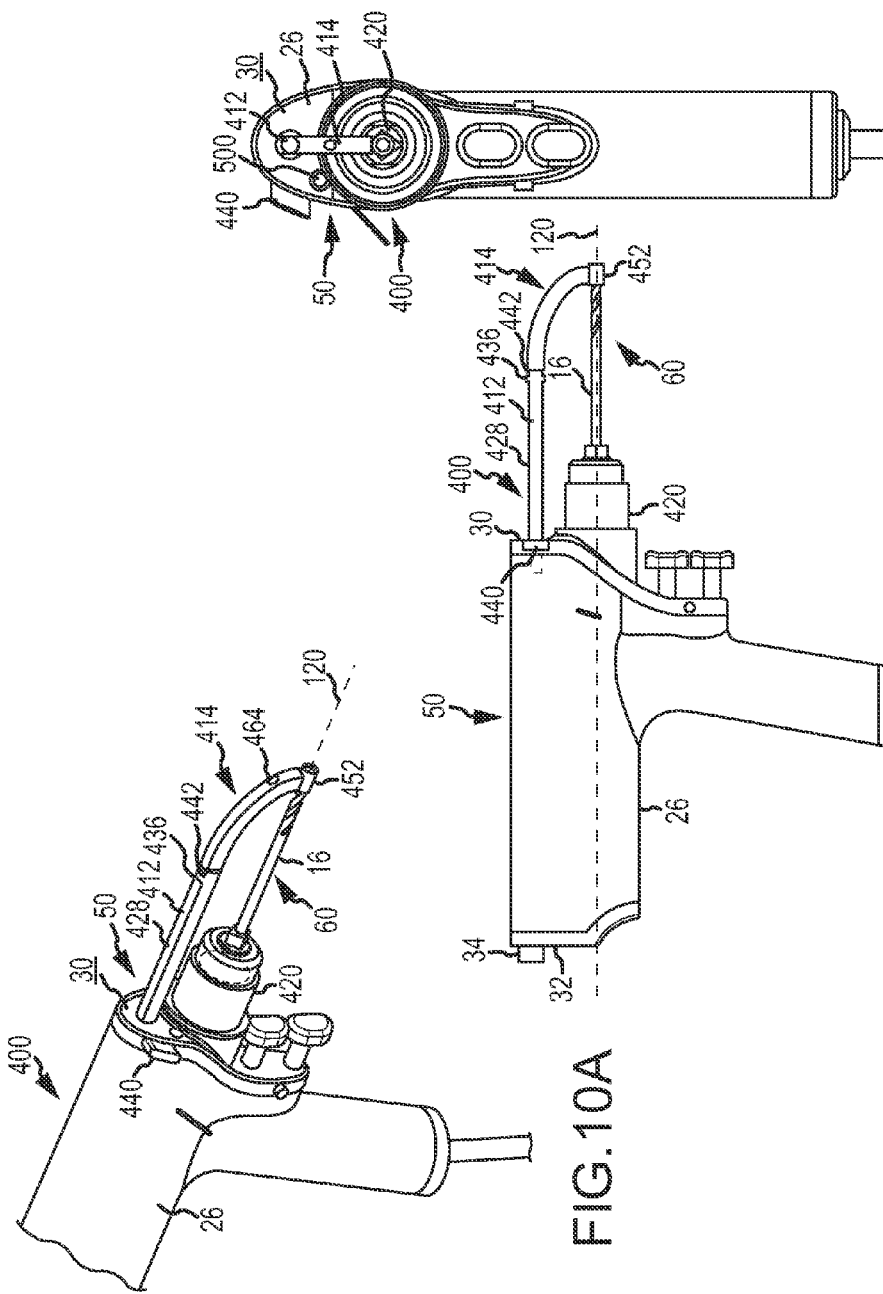
FIGS. 10A-10C are perspective, side, and front views, respectively, of an embodiment of a drill comprising a drill bit penetration measurement system.

Referring to the drawings in detail, where like numerals indicate like elements throughout there is shown in FIGS. 2-8 a first preferred embodiment of the drill bit penetration measurement system generally designated 100, and hereinafter referred to as the "measurement system" 100, in accordance with the present invention. The measurement system 100 is for determining, with respect to a reference point (not shown), a depth of penetration of the leading edge 16a of a rotating drill bit 16 in a bore when the leading edge 16a of the drill bit 16 passes from a first medium having a first density to a second medium adjacent the first medium and having a second density. The drill bit 16 is rotatably driven by a drive 24 in a drill housing 26 of any typical well known surgical drill. In this regard and as may be appreciated below, a measurement system 100 may be provided with an existing surgical drill (e.g., as a retrofit). In a further embodiment described in greater detail below, a measurement system 400 may be provided that is at least partially integrated into a drill 50 (e.g., as shown in FIGS. 10A-10C).

Preferably the first and second media are the hard outer cortex 12 and a medium such as air or other anatomical structure (not shown) surrounding the outer surface of the cortical bone 10 and the bore is either the bicortical bore 18 or the unicortical bore 20 being drilled in the cortical bone 10. (See FIGS. 1A-1B). However, those skilled in the art will understand from the present disclosure that the first and second media can be the hard outer cortex 12 and the soft inner medullary layer 14 of the cortical bone 10 or any adjacent media of different density without departing from the scope of the invention. The artisan will also understand that the reference point is a fixed point relative to which the displacement of the leading edge 16a of the drill bit 16 is measured and may correspond to an initial position of the measurement system 100 or portion thereof as further discussed below.

Referring to FIGS. 2, 7A, 7B and 7C, the measurement system 100 comprises a drill bit displacement measurement assembly 102, a drill bit load measurement assembly 104, and a controller assembly 106. The displacement measurement assembly 102 is connected to the drill housing 26. The connection can be made by a variety of well known mounting methods such as a mount that clamps to the displacement measurement assembly 102 and is attached to the drill housing 26 by one or more threaded fasteners. Alternative methods such as welding or adhesive bonding could also be used. The displacement measurement assembly 102 has a first sensor 108 that outputs a first signal 108s representative of a displacement, with respect to the reference point, of the leading edge 16a of the drill bit 16 in the bore being drilled. The displacement measurement assembly 102 preferably has an extension 110 that is displaceable along a longitudinal axis. The extension 110 has a distal end 110a that can be placed in registry with the reference point when the leading edge 16a of the drill bit 16 is positioned at the entry point, such as the entry point 18a of the bicortical bore 18 or the entry point 22a of the unicortical bore 20 shown in FIGS. 1A-1B and maintained in registry with the reference point throughout the drilling process. The reference point can be any anatomical structure proximal to the desired location of the bore to be drilled. The extension 110 has a proximal end 110b that is attached to the first sensor 102. Preferably the sensor 102 is a linear variable differential displacement transducer ("LVDT").

Referring to FIGS. 3A and 3B, the drill bit load measurement assembly 104 comprises a housing 112, a thrust assembly 114 about which the housing 112 is rotatable, a drill chuck 116 and a second sensor 118. The housing 112 has an axis of rotation 120 and is removably connected to the drive 24 for rotation thereby. Preferably, the housing 112 has a generally cylindrical-like shape and has a chamber 122 extending the length thereof for containing a portion of the thrust assembly 114 and a portion of the drill chuck 116. Preferably, but not necessarily, the housing 112 also has a proximal end 112a with an outer diameter sized for being secured in a drive chuck 28 of the drive 24. Those skilled in the art will understand from this disclosure that the drive chuck 28 can be any well known surgical drill chuck through which surgical instruments are insertable.

The thrust assembly 114 is preferably a tube 124 with a bore 126 therethrough. The bore 126 has a piston 128 moveable therein. The tube 124 has a first portion 124a having a first outer diameter and a second portion 124b having a second outer diameter less than the first outer diameter. Similarly, the bore 126 has a first portion 126a having a first inner diameter and a second portion 126b having a second inner diameter less than the first inner diameter. Preferably, the piston 128 is in the first portion 126a of the bore 126. The second portion 124b of the tube 114 extends beyond the proximal end 112a of the housing 112. The thrust assembly 114 is connected to the housing 112 by a first bearing 130 and to the drill chuck 116 by a second bearing 132, preferably connected to the piston 128. Preferably, the first and second bearings 130, 132 are thrust bearings suitable for use in a surgical environment. Alternatively, the first and second bearings 130, 132 could be any device that permits the housing 112 and the drill chuck 116 to rotate with respect to the thrust assembly 114 and allows a force applied to the leading edge 16a of the drill bit 16 to be transferred to the thrust assembly 114. Preferably, but not necessarily, the thrust assembly 114 also is journaled with the housing 112 by a third bearing 134.

The drill chuck 116 is connected to the housing 112 for rotation therewith and to the thrust assembly 114 for rotation with respect thereto. The drill chuck 116 is moveable in translation along the axis of rotation 120 of the housing 112. Preferably, the drill chuck 116 is a conventional surgical drill chuck having a proximal end 116a within the chamber 122 of the housing 112. The drill chuck is connected to the housing 112 by a tab 136 extending radially outwardly from the proximal end 116a of the drill chuck 116. The tab 136 extends into a corresponding slot 138 in the housing and is moveable therein in translation along the axis of rotation 120 of the housing 112. Preferably, but not necessarily, the drill chuck 116 has diametrically opposed tabs 136. Those of ordinary skill in the art will understand from the present disclosure that tabs 136 can be removably attached to the drill chuck 116 by a threaded fastener (not shown) to facilitate insertion of the proximal end 116a of the drill chuck into the housing 112. The proximal end 116a of the drill chuck 116 additionally has a projection 140 that extends into the bore 126 of the thrust assembly 114 and is connected by the second bearing 132 to the piston of the thrust assembly 114.

The second sensor 118 in connected to the thrust assembly 114 and outputs a second signal 118s representative of a force applied to the leading edge 16a of the drill bit 16. As shown in FIG. 3A, in one preferred embodiment of the present invention, the second sensor 118 is a hydraulic pressure transducer and a portion of the bore 126 forms a hydraulic chamber 142 connecting the second sensor 118 with the piston 128. As shown in FIG. 4A, in another preferred embodiment of the present invention, the second sensor 118' is a load cell, such as a piezo-electric device, adjacent the piston 128 and a portion of the bore 126 forms a conduit 142' through which passes an electrical conductor 144 connecting the piezo-electric device to the controller assembly 106.

Figure 2:
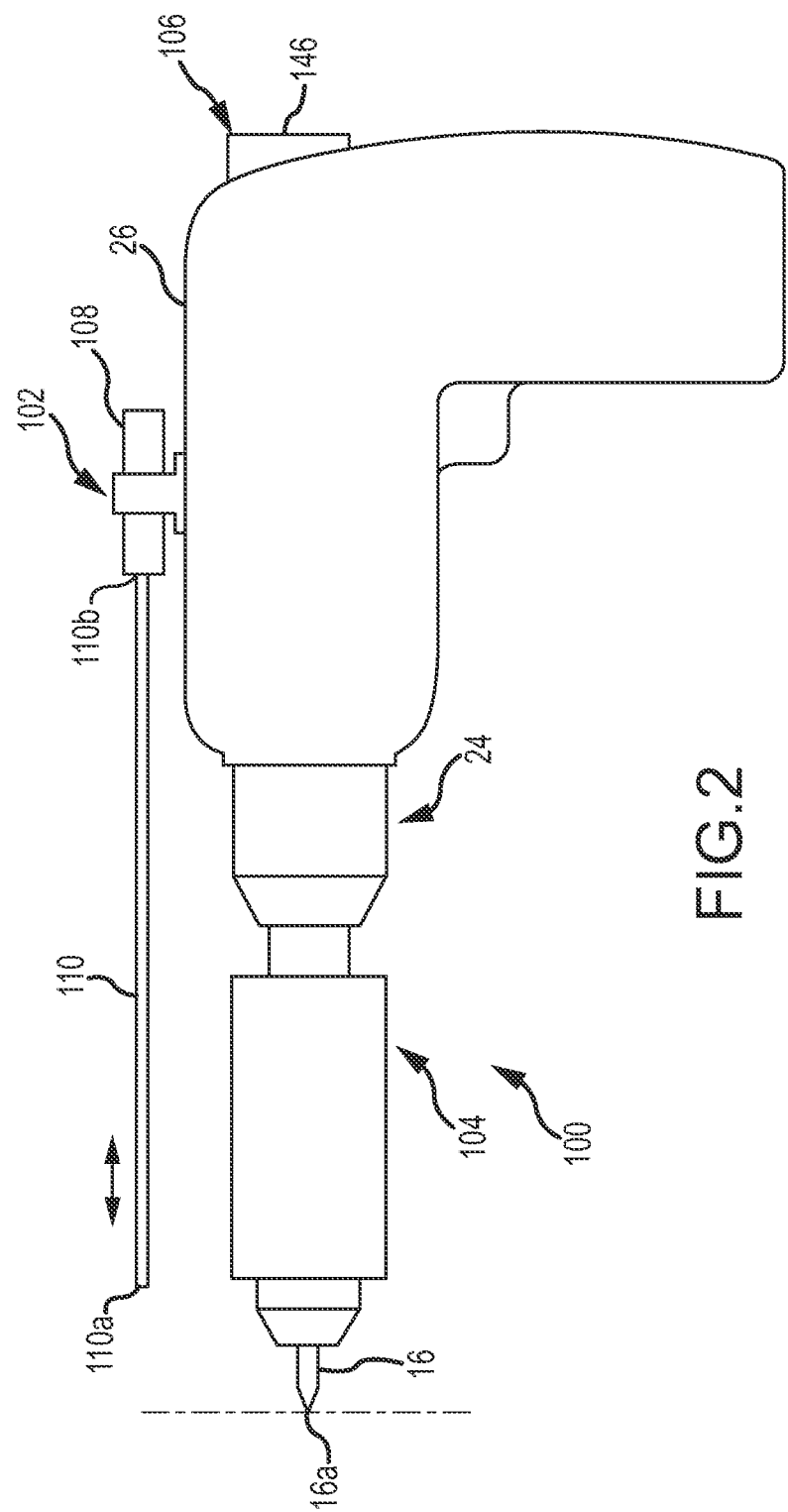
FIG. 2 is an elevation view, partially in cross section of an embodiment of a real-time, drill bit penetration measurement system.
Figure 3:
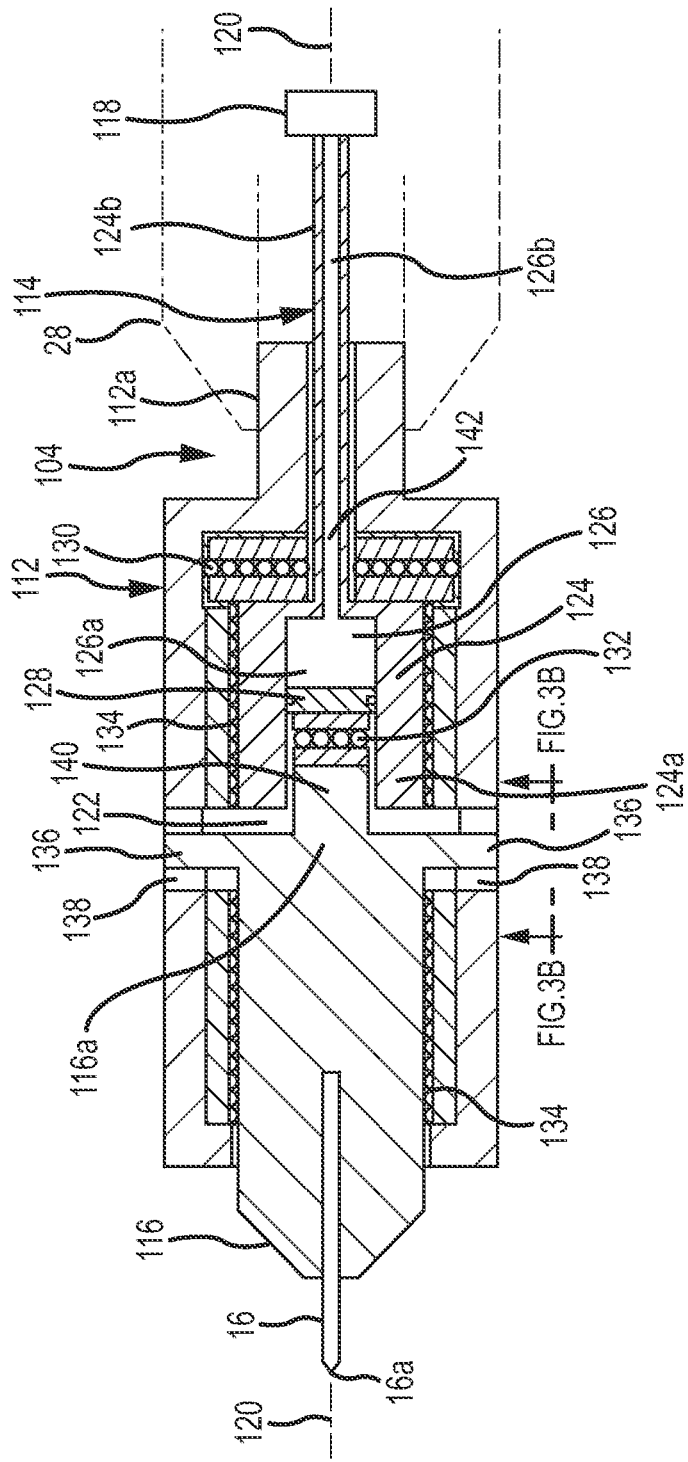
FIG. 3A is an enlarged sectional view of the embodiment of the drill bit load measurement assembly of FIG. 2.
FIG. 3B is a sectional view of a portion of the drill bit load measurement assembly taken along the line 3B-3B of FIG. 3A.
Figure 4:
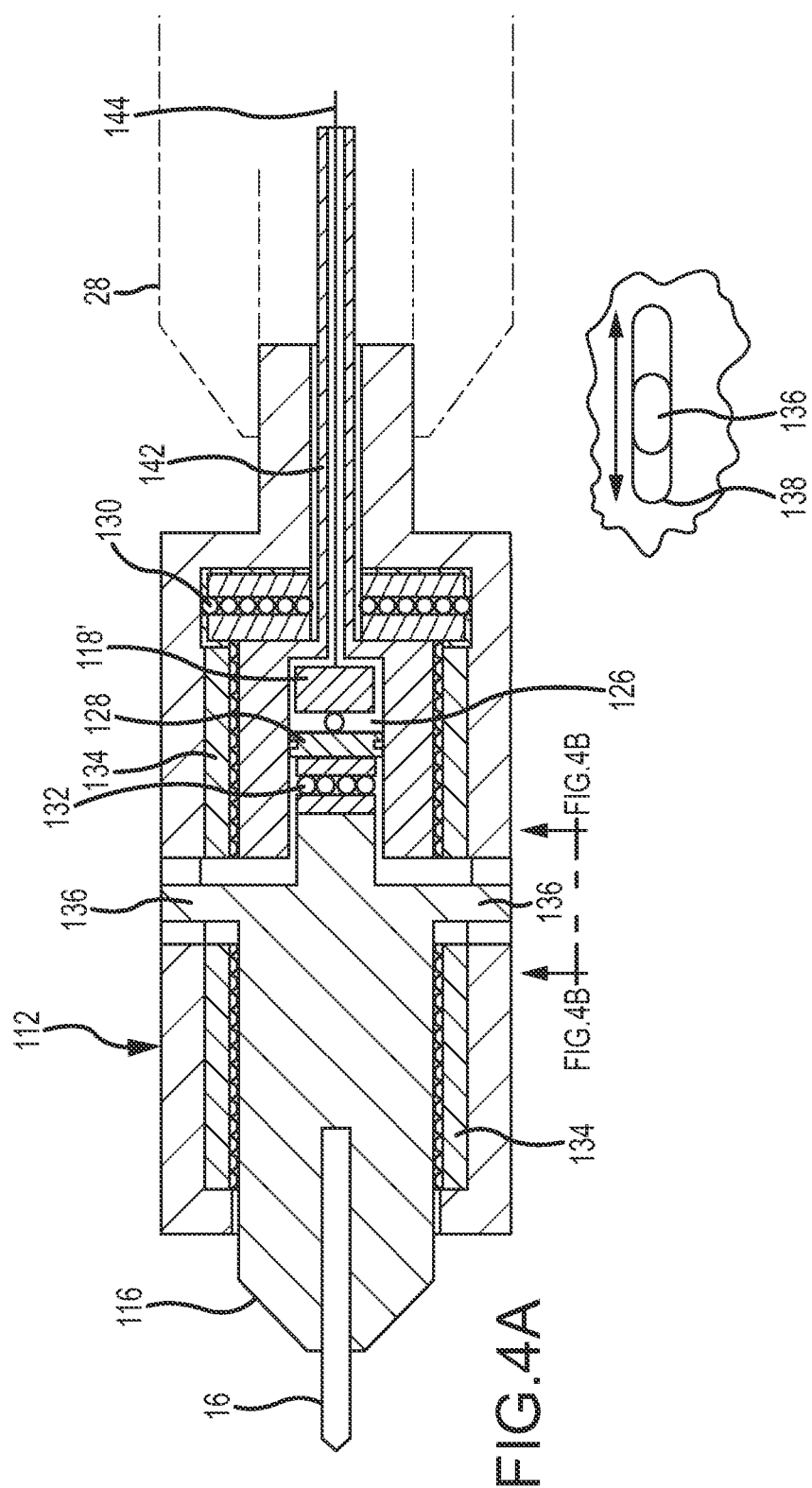
FIG. 4A is an enlarged sectional view of an embodiment of the drill bit load measurement assembly of FIG. 2.
FIG. 4B is a sectional view of a portion of the drill bit load measurement assembly taken along the line 4B-4B of FIG. 4A.
Figure 5:
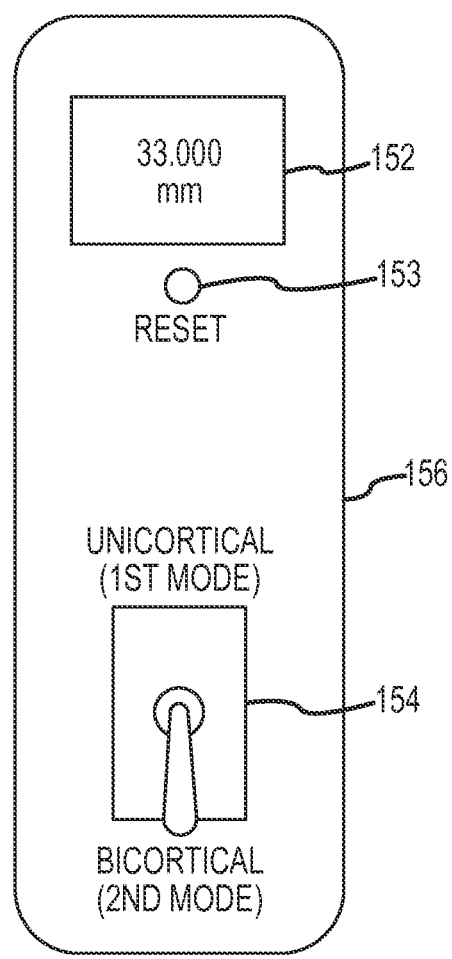
FIG. 5 is an elevation view of an embodiment of a control panel of a controller assembly of FIG. 2.
Figure 6:
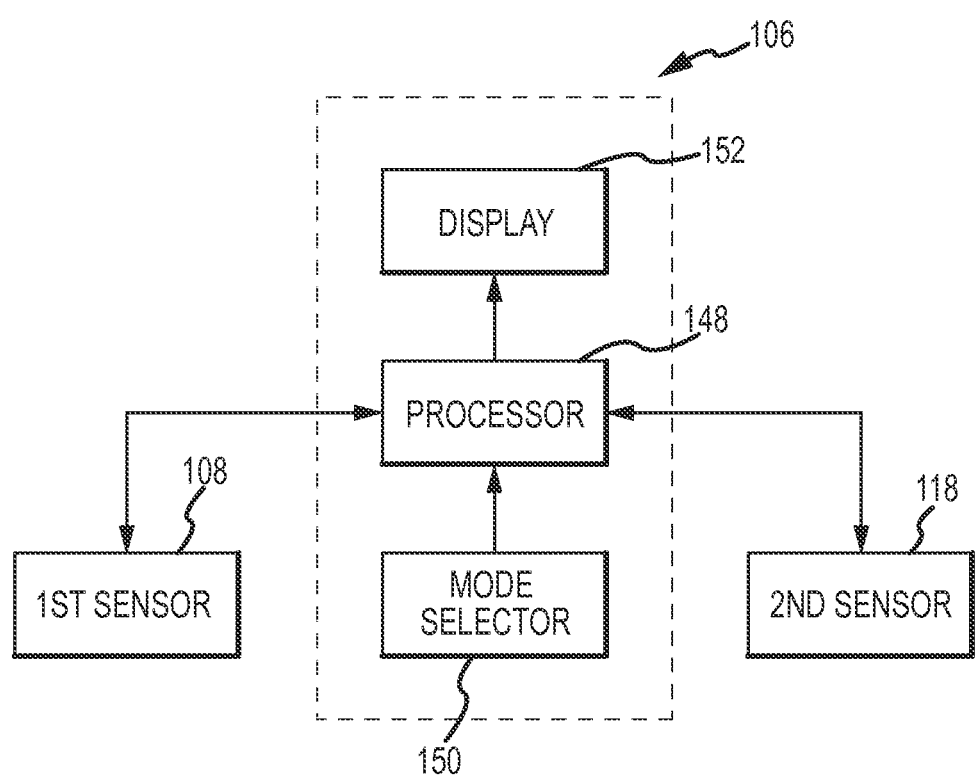
FIG. 6 is a schematic block diagram of the controller assembly of FIG. 2 and the inputs and outputs of the controller assembly.
Figure 7:
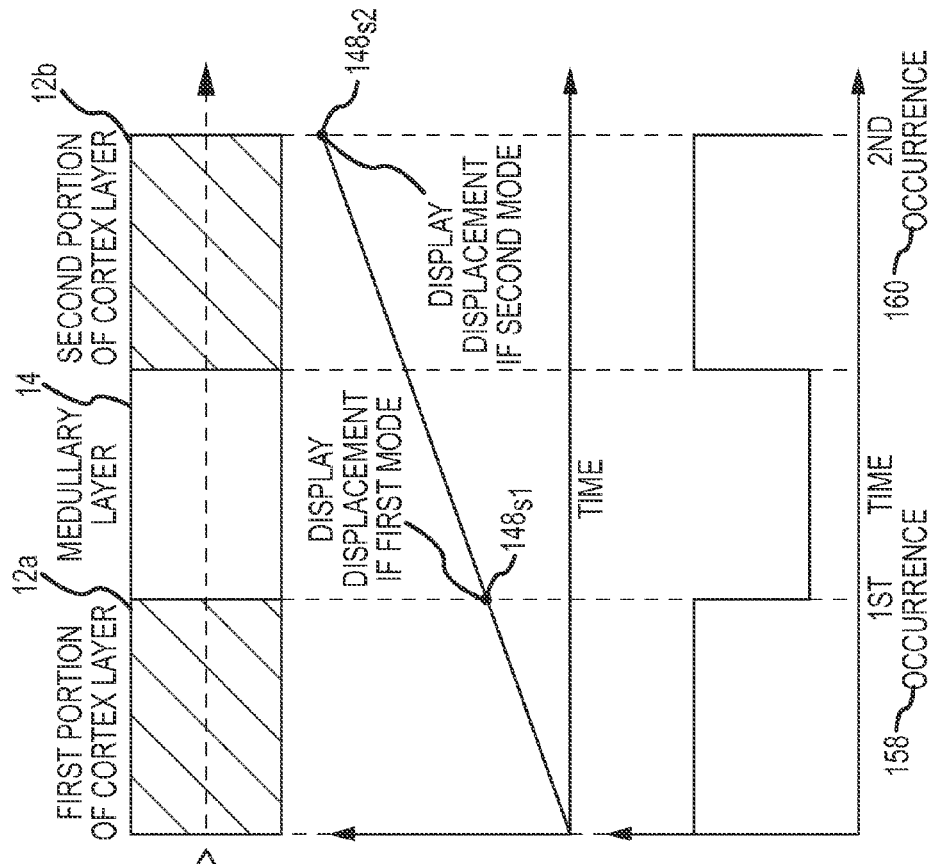
FIGS. 7A, 7B, and 7C are diagrams illustrating the position of the drill bit of FIG. 2 in bicortical bore of FIG. 1B and the corresponding output of the first and second sensors of the displacement and load measurement assemblies of FIG. 2.

Referring to FIGS. 2 and 5-6, the controller assembly 106 is in electrical communication with the first sensor 108 and the second sensor 118. In an embodiment, the controller assembly 106 has a controller housing 146 integral with the drill housing 26. However, with further reference to FIG. 21A, the controller housing 146 may also be provided as a remote unit. The controller assembly 106b includes a processor 148 in electrical communication with the first and second sensors 108, 118 and with a mode selector 150 having a mode selector switch 154 and a display 152 having a reset button 153. The display 152, the reset button 154 and the mode selector switch 154 may be mounted in a panel 156 of the controller housing 146. Alternatively, the display 152 or the reset button 153 or the mode selector 154 or any combination thereof could be separately housed in the remote control unit that communicates with the first and second sensors 108, 118 by a wired or wireless link. The display 152 is for indicating the measured displacement of the leading edge 16a of the drill bit 16 to the user. The display 152 is controlled by the processor 148. The display 152 may continuously indicate the changing displacement of the leading edge 16a of the drill bit 16 during the drilling of a bore and may also indicate the length of the bore at the when the drill bit 16 passes from one medium to another.

Figure 21B:
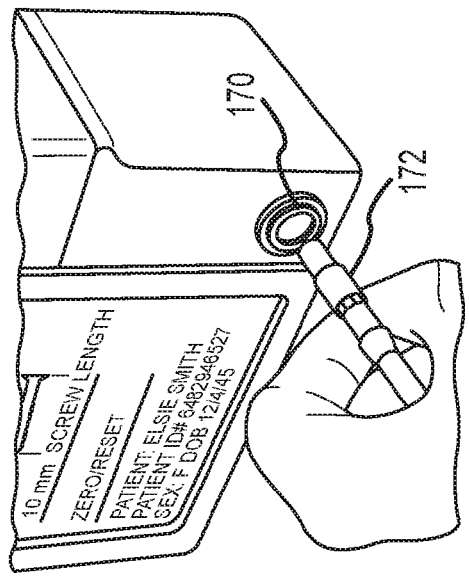
FIGS. 21A and 21B depict an embodiment of a controller for use in operation of a drill having a drill bit penetration measurement system.
Figure 21A:
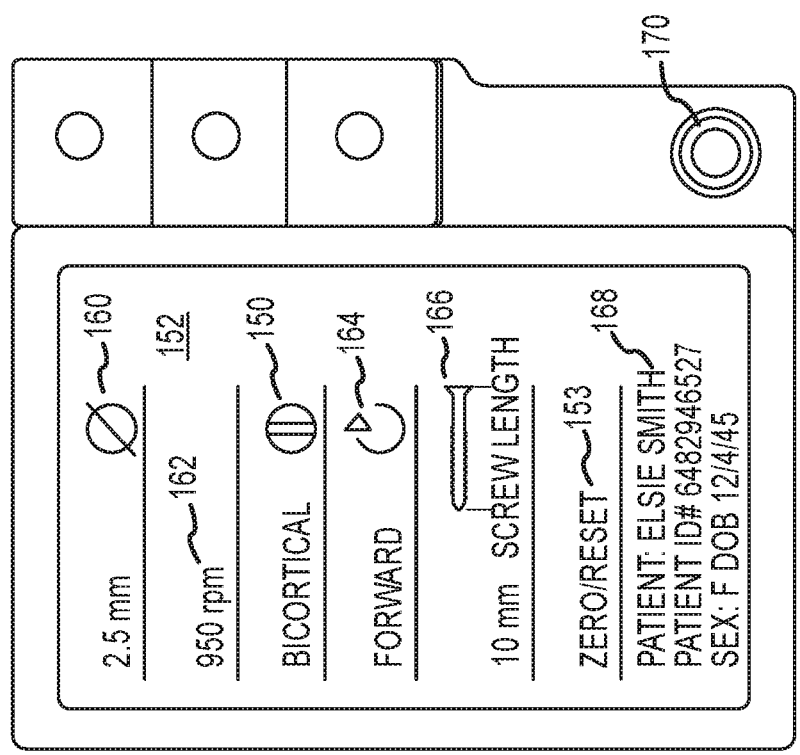

For instance, with continued reference to FIGS. 21A and 21B, the display 152 may be a touch sensitive display (e.g., a resistive or capacitive type touch screen display). The display 152 may include an indication of a bore diameter 160, the drill speed 162, a drill direction 164, and a screw size indicator 166. The display 152 may also include patient information 168. The controller unit 106 may include a port 170 for engagement of a wired plug connection 172 with the drill 50. In this regard, the drill 50 may be connected to the controller assembly 106 to supply power to the drill 50 and communicate data between the drill 50 and the controller assembly 106

Referring to FIGS. 1, 5-6, 7A, 7B, and 7C, the processor 148 is configured to operate in a first mode for drill bit penetration measurement in unicortical bore drilling. In the first mode the processor 148 is configured to output a third signal $148s_1$ representative of the depth of penetration of the leading edge 16a of the drill bit 16 when the leading edge 16a of the drill bit 16 passes from the first medium to the second medium. The third signal $148s_1$ is based on the first and second signals 108s, 118s. Preferably, the third signal $148s_1$ is output upon a first occurrence 158 of a second time derivative of the first signal 108s being greater than zero and a first time derivative of the second signal 118s being less than zero. In other words a positive acceleration of the drill bit 16 and a concurrent reduction in the force applies to the leading edge 16a of the drill bit 16 trigger the first occurrence 158. At the time of the first occurrence 158, the third signal $148s_1$ corresponds to the length of the unicortical drill path.

Preferably, but not necessarily, the processor 148 is also configured to operate in a second mode for drill bit penetration measurement in bicortical bore drilling and the mode selector 150 and mode selector switch 154 are for selecting between the first and second modes. The second mode of operation is directed to the case where the first medium is the cortical bone 12 surrounded by a second medium, such as the air or tissue surrounding the outer surface of the cortical bone 12, and the first medium encloses a third medium, such as the soft medullary layer 14, having a third density. In the second mode, the processor 148 is configured to output the third signal $148s_2$ in response to a second occurrence 160 of the second time derivative of the first signal 108s being greater than zero and the first time derivative of the second signal 118s being less than zero and corresponds to the length of the bicortical drill path. Accordingly, the third signal $148s_2$ is output after the second time the drill bit 16 accelerates with a concurrent reduction in the force applied to the leading edge 16*a* of the drill bit 16.

Additionally or alternatively, the third signal 148s (collectively referring to $148s_1$ and $148s_2$ referenced above) may be at least partially based on additional parameters other than the first signal 108s and second signal 118s. For instance, in at least some embodiments, the third signal 148s may be at least partially based on a parameter associated with the rotation of the drill bit 16. For instance, the speed of the drive 24 turning the drill bit 16, the torque applied to the drill bit 16 by the drive 24, or another appropriate parameter regarding the rotation of the bit 16 may be utilized in outputting the third signal 148s. Further still, parameters such as the diameter of the drill bit 16, the bone to be drilled, or other appropriate parameters may be utilized in determining the third signal 148s.

Furthermore, the generation of the third signal 148s may at least partially be customized based on the patient. In this regard, information regarding the patient may be provided to the controller assembly 106 and utilized by the processor 148 in determining the third signal 148s. For instance, a patient's age, sex, and/or other demographic information may be provided. As may be appreciated, the demographic data of the patient may provide a correlation to expected bone density or other parameter regarding an expected property of the patient's anatomy based on the demographic data of the patient. In this regard, the demographic data may be used to correlate an expected parameter associated with the patient's anatomy (e.g., bone density) that may be used as a factor in generation of the third signal 148s. In addition, direct measurement of an anatomical parameter (e.g., bone density) for a given patient may be provided directly to the controller assembly 106, thereby potentially eliminating the need to estimate the parameter based on demographic data.

Figure 1B:
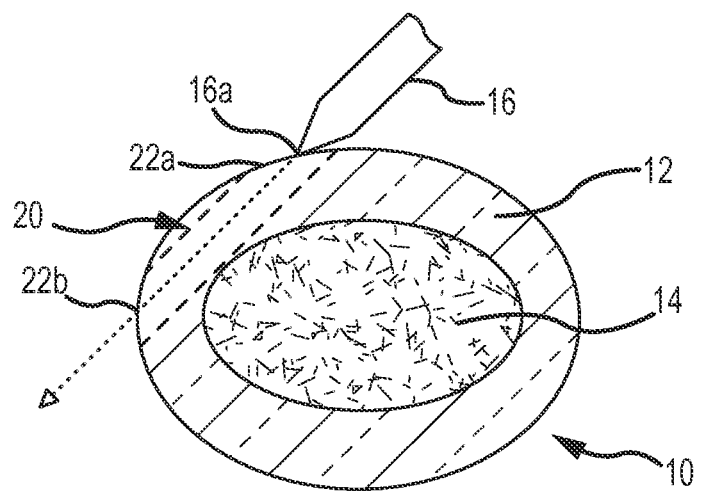
FIG. 1B is a sectional view of a bone illustrating a prior art method of using a drill mechanism to create a unicortical drill path through the outer layer of a cortical bone.
Figure 8:
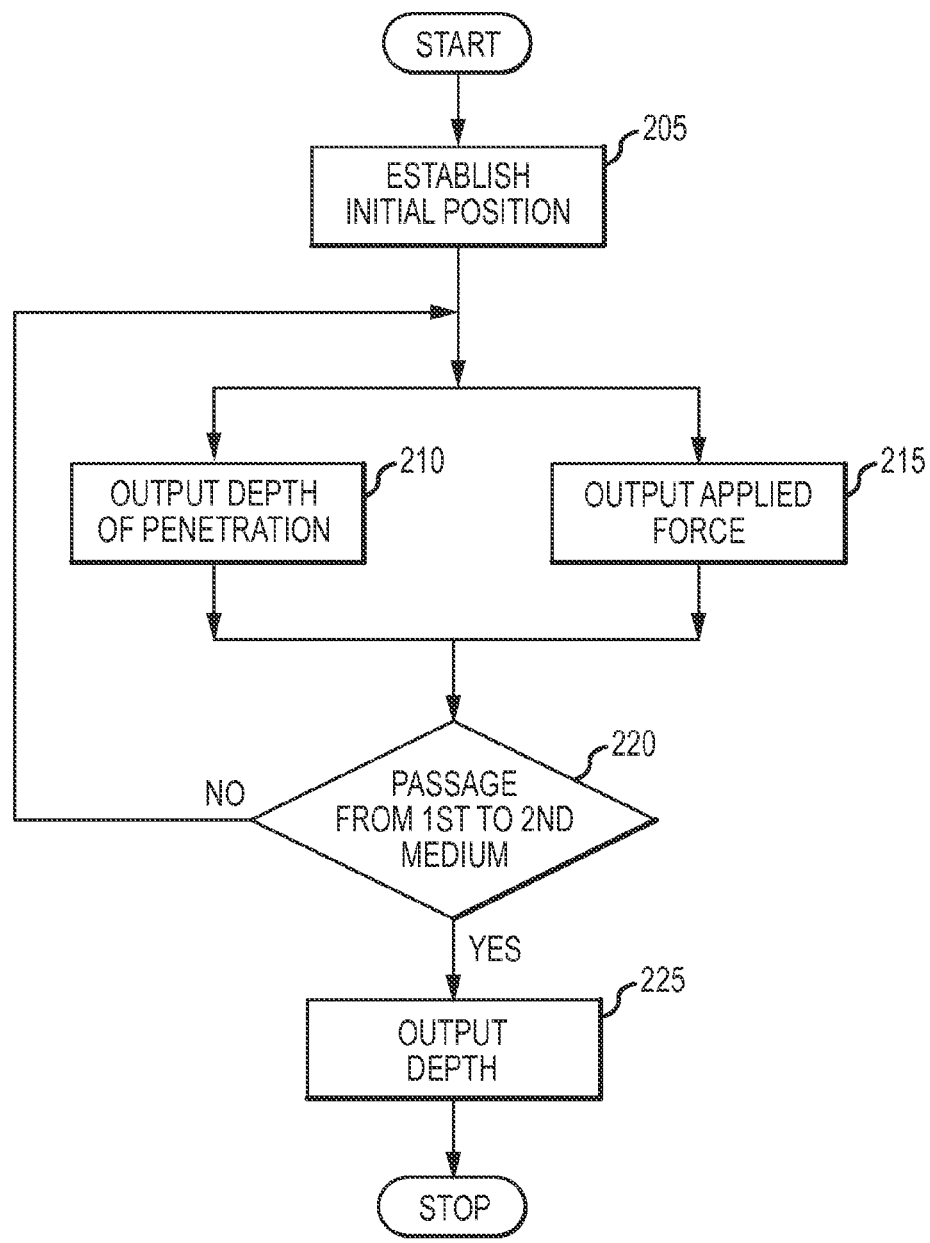
FIG. 8 is a flow diagram of an embodiment of a method for determining the depth of penetration of a drill bit.

Referring to FIG. 8, there is shown a block diagram of a first preferred method for determining, with respect to a reference point, the depth of penetration of the leading edge 16*a* of a rotating drill bit 16 in a bore when the leading edge 16*a* of the drill bit 16 transitions from a first medium having a first density, such as the hard outer cortex 12 of a cortical bone 10, to a second adjacent medium having a second density, such air or tissue surrounding the outer surface of the cortical bone 10. (FIG. 1B).

An initial position of the leading edge 16*a* of the drill bit 16 relative to the reference point is established (Step 205). The initial position may be established by placing the leading edge 16*a* of the drill bit 16 against the outer surface of the cortical bone to be drilled and by extending the distal end 10*a* of the extension 110 of the displacement measurement assembly 102 to the reference point, such as an anatomical structure proximal to the desired location of the bore to be drilled. As will be appreciated in the discussion of the embodiments below, the reference point may also be established by a bushing member of a drill bit assembly that is engaged with a displacement sensing arm of a displacement sensor. With the leading edge 16*a* of the drill bit 16 and the measurement system reference point in the above positions (i.e., aligned at a surface of the medium to be drilled), the measured displacement of the drill bit 16 is set to zero by pressing the reset button 153. Upon commencement of drilling, a first signal representing the depth of penetration of the leading edge 16*a* of the rotating drill bit 16 in the bore is output (Step 210). A second signal representing a force applied to the leading edge of the drill bit is output (Step 215). A third signal based on the first and second signals and representative of the depth of penetration of the leading edge of the drill bit when the leading edge of the drill bit passes from the first medium to the second medium is output (Step 220). Preferably, the third signal is output when the second time derivative of the first signal is greater than zero and a first time derivative of the second signal is less than zero.

The third signal may be accompanied by (e.g., include) an alert that may be perceivable by a user of the drill. As such, upon determination that the drill has passed through the bone (e.g., as described above), the alert may provide feedback to the user that the bone has been drilled through. As such, the alert may be an auditory alert such as a tone or the like. In another embodiment, the alert may be a change in the speed of the motor of the drill. For instance, the drill may be slowed such that the user may be alerted to the fact that the drill has passed through the bone. Further still, the drill may be stopped at the occurrence of the third signal. It may be appreciated that any other user perceivable alert may be provided including, for example, a visual, tactic, or other type of user perceivable feedback.

Figure 9:
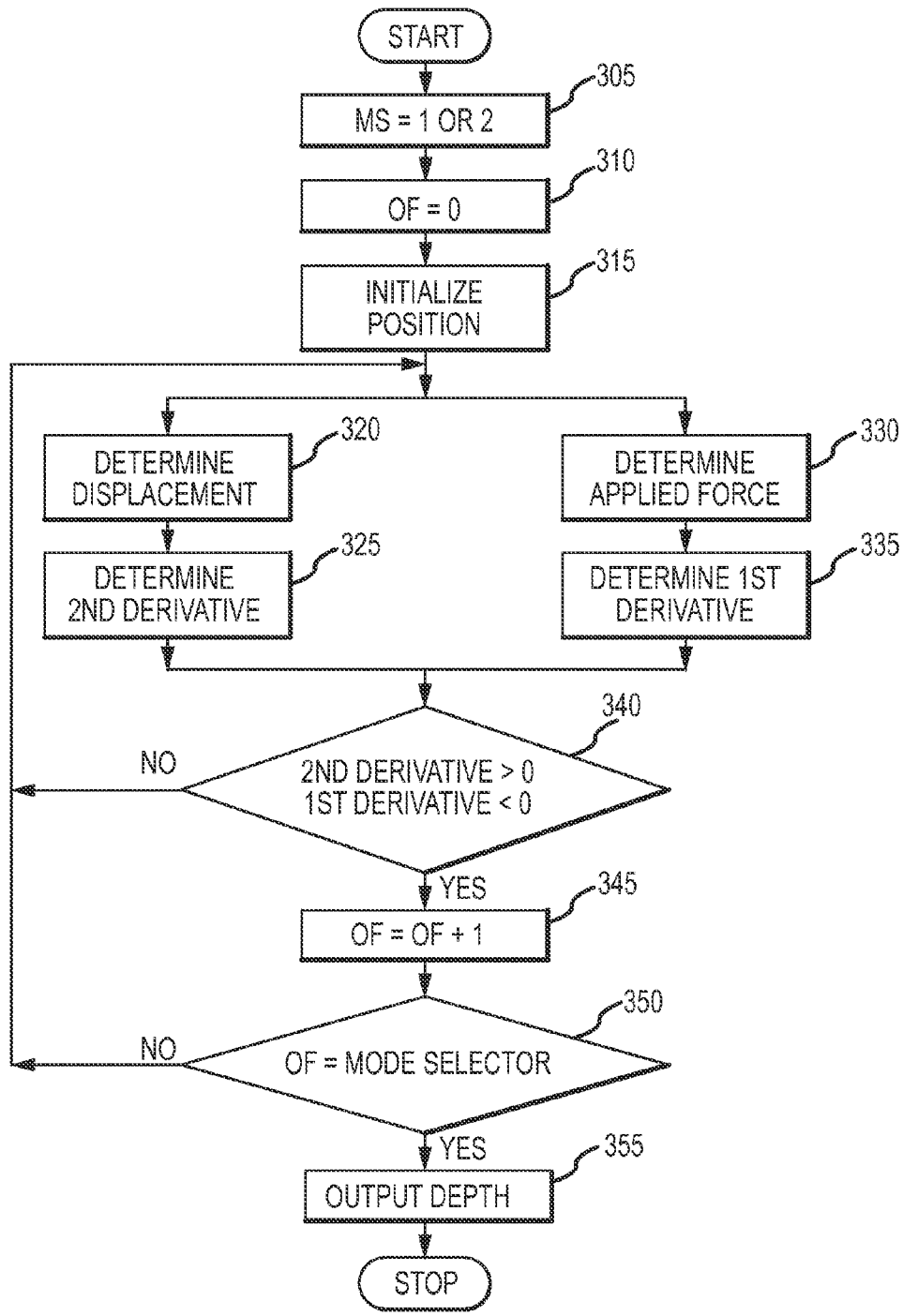
FIG. 9 is a flow diagram of an embodiment method for determining the depth of penetration of a drill bit.

Referring to FIG. 9, there is shown a block diagram of a second preferred method for determining, with respect to a reference point, the depth of a drilled unicortical bore 20 or a drilled bicortical bore 18. (FIGS. 1A and 1B). The mode selector switch 15 (MS) is set to the value "1" if a unicortical bore 20 is being drilled or set to the value "2" if a bicortical bore 18 is being drilled (Step 305). An occurrence flag (OF) is set to zero (Step 310). An initial position of the leading edge 16*a* of the drill bit 16 relative to the reference point is established (Step 315), preferably in a manner similar to Step 205 discussed above. The displacement of the leading edge 16*a* of the drill bit 16 and the force applied to the leading edge 16*a* of the drill bit 16 are continuously determined, (Steps 320 and 330, respectively). The second time derivative of the displacement of the leading edge 16*a* of the drill bit 16 ("drill bit acceleration") is determined (Step 325) and the first time derivative of the force applied to the leading edge 16*a* of the drill bit 16 ("change in applied force") is determined (Step 335). The occurrence flag is updated by adding one to its present value (Step 345) if the drill bit acceleration is positive and the change in applied force is negative (Step 340), otherwise determination of the displacement and the applied force continues. The depth of the bore is output (Step 355) if the value of the occurrence flag is equal to the value of the mode selector (Step 350), otherwise determination of the displacement and the applied force continues.

The components used to construct the present invention may consist of a variety of materials that are customarily used in the manufacture of surgical drills. One having ordinary skill in the art will readily appreciate the materials that most desirably may be used to construct the present invention. In a preferred embodiment, however, the drilling mechanism, drill bit displacement measurement assembly, the drill bit load measurement assembly and the structural elements of the controller assembly may be constructed of a combination of polymeric materials (e.g., high strength plastic), polymers and stainless steel.

Furthermore, it may be appreciated that the spacing of the extension 110 of the displacement sensor 102 from the drill bit 16 may introduce the potential for errors or other disadvantages in determining the displacement of the drill bit 16 relative to the reference point. For instance, as the extension 110 may contact a structure that is offset from the contact point between the leading edge 16a of the drill bit 16 and the medium to be drilled. Accordingly, any movement between the structure contacted by the extension 110 and the medium to be drilled may be falsely registered as relative movement of the drill 16 with respect to the reference point. Furthermore, there may not be a rigid structure to contact adjacent to the medium to be drilled, leading to displacement of the structure contacted by the extension 110 (e.g., such as in the case where the extension 110 may contact soft tissue adjacent to the medium to be drilled given the offset from the location to be drilled). Furthermore, the offset nature of the extension 110 relative to the contact between the drill bit 16 and the medium to be drilled may lead to other complications such as having to expose a greater surface of the medium to be drilled, which may adversely affect patient outcomes.

As such, an improved embodiment of a drill with an improved displacement sensor including a displacement sensing arm that extends from the drill may be provided. For example, such a displacement sensing arm may be provided that may coordinate with a bushing member of a drill bit assembly that may be used with the drill. In this regard, the bushing may move along the drill bit in a direction corresponding to the axis of rotation of the drill bit. Upon engagement of the bushing and the displacement sensing arm, the bushing and displacement sensing arm may undergo corresponding movement. As such, the bushing may be disposed in contact with the medium to be drilled when the leading edge of the drill bit is in contact with the medium. As such, a reference point may be established when the bushing and leading edge of the drill bit are both in contact with the medium to be drilled. As the bushing is located adjacent to (e.g., partially or fully surrounding the drill bit), the bushing may facilitate contact with the medium at or very near the location to be drilled prior to creating a bore as described above. In this regard, the reference point may be more accurately maintained as the bushing may contact at least a portion of a periphery of the bore created in the medium drilled. That is, the bushing may remain in intimate contact with the medium to be drilled adjacent to the bore created. This may prevent false displacement readings attributable to the foregoing problems associated with an offset extension 110. Furthermore, the amount of contact of the drill may be localized at the location to be drilled, thus allowing for potentially less intrusion when performing drilling operations.

For example, with additional reference to FIGS. 10A-10C and 11, an embodiment of a drill 50 comprising an embodiment of a measurement system 400 is shown. The drill 50 may be adapted for use with a drill bit assembly 60 (shown in FIG. 12) that may include a bushing 452. The drill 50 may integrally comprise at least some components of the measurement system 400 to facilitate operation of the measurement system 400 in connection with the drill 50 (e.g., which may be according to the description above regarding measurement system 100). For example, at least a portion of a displacement sensor 410 may be integrated into a housing 26 of the drill 50. In this regard, the displacement sensor 410 may include a depth sensing arm 412 that is specifically adapted for engagement with a bushing 452 of a drill bit assembly 60 that may be engaged by the chuck 420 of the drill 50.

In this regard, the depth sensing arm 412 may be used to establish a reference point from which displacement of the drill bit 16 may be measured as described above. In this regard, as follows herein, a general description of the features and operation of the drill 50 used in conjunction with the drill bit assembly 60 is provided.

Figure 11:
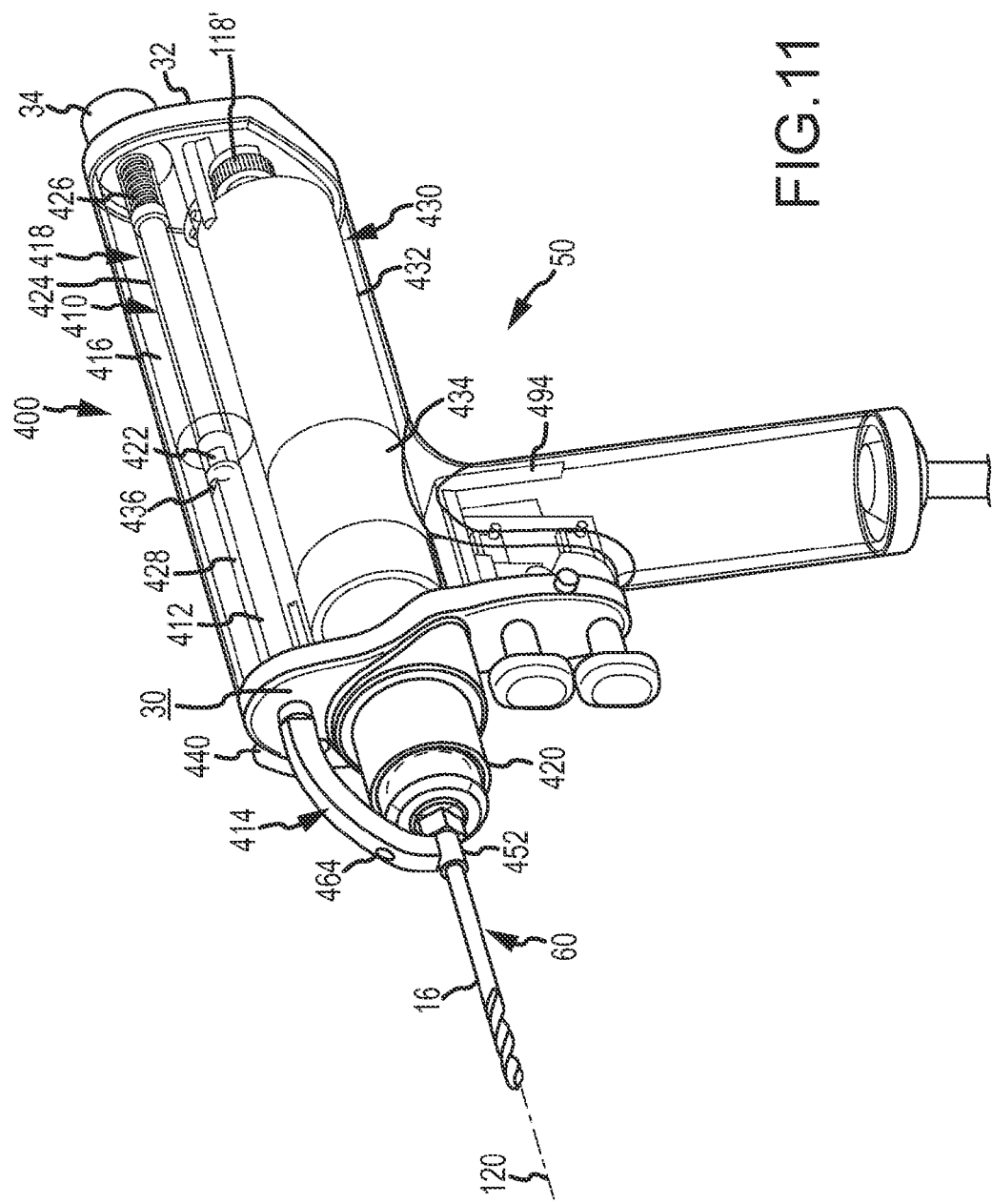
FIG. 11 is a perspective view with a partial cutaway of a drill body of an embodiment of a drill comprising a drill bit penetration measurement system.

As may be appreciated in FIGS. 10A-10C, the displacement sensor 410 may include a depth sensing arm 412 that may extend from the drill housing 26. For example, the depth sensing arm 412 may extend distally (e.g., from a distal face 30 of the drill housing 26) in a direction corresponding with the direction in which the drill bit 16 extends from a chuck 420 of the drill 50. At least a portion of the displacement sensing arm 412 may extend from the drill housing 26 parallel to an axis of rotation 120 of the drill 50. The depth sensing arm 412 may also include a distal portion 414 that is adapted to engage a bushing 452 provided with the drill bit assembly 60 shown in FIG. 12. As used herein, distal may correspond to a direction from the drill 50 toward the leading edge 16a of the drill bit 16 and proximal may correspond to a direction from the leading edge 16a of the drill bit 16 toward the drill 50. In this regard, at least a portion of the depth sensing arm 412 (e.g., the distal portion 414) may be adapted to engage the bushing 452 of the drill bit assembly 60 as will be described in more detail below. In any regard, at least a portion of the depth sensing arm 412 may extend into the housing 26. With further reference to FIG. 11, the housing 26 may contain a coil 416. As such, a proximal end 418 of the displacement sensing arm 412 may interface with the coil 416 of the displacement sensor 410 that may be disposed within the drill housing 26.

Specifically, in FIG. 11, the depth sensing arm 412 is shown in a retracted position relative to the drill bit 16. As such, this retracted position shown in FIG. 11 may occur when the drill bit 16 is advanced relative to the bushing 452 during drilling (e.g., such that the portion of the drill bit extending beyond the distal edge of the bushing 452 would be disposed in the medium to be drilled). In this regard, the proximal end 418 of the displacement sensing arm 412 is disposed within the coil 416 of the displacement sensor 410. Accordingly, the displacement sensor 410 may comprise an LVDT sensor as described above that is adapted to sense the position of a core 422 relative to a coil 416. The displacement sensing arm 412 may incorporate a core 422 at the proximal end 418 thereof. Accordingly, as the proximal end 418 of the displacement sensing arm 412 is moved relative to the coil 416, the location of the core 422 may be determined to provide an output corresponding to the position of the core 422, and in turn the displacement sensing arm 412 relative to the drill housing 26. That is, the depth sensing arm 412 may be displaceable relative to the coil 416 such that the displacement sensor 410 may be operable to sense a change in position of the depth sensing arm 412 relative to the drill housing 26 and output a measure of the displacement that may be used as described above in determining a depth of a bore. In an embodiment, the total measurable travel of the core 422 relative to the coil 416 may be at least about 2.5 in (6.4 cm). Furthermore, the resolution of the output of the displacement sensor 410 may be about 0.1% (e.g., about 0.002 inches (0.06 mm) for a sensor having a total measureable travel of 2.5 inches).

While a LVDT displacement sensor is shown and described in relation to the drill 50 shown in the accompanying figures, it may be appreciated that other types of displacement sensors may be provided. For instance, the sensor may provide for the absolute or relative measurement of the position of the distal end 418 of the displacement sensing arm 412 to provide a displacement measure. For instance, in another embodiment, an optical displacement sensor may be provided. Other types of displacement sensors are also contemplated such as, for example, a capacitive displacement sensor, ultrasonic sensors, Hall effect sensors, or any other sensors known in the art capable of outputting an absolute or relative position measure.

In an embodiment, the coil 416 may define a passage 424 extending at least partially through the housing 26. Specifically, the passage 424 may extend from a proximal face 32 of the housing 26 to the distal face 30 of the housing 26. That is, the passage 424 may extend entirely though the housing 26. An end cap 34 may be provided that is operable to close the proximal end of the passage 424 at the proximal face 32 of the drill housing 26. Furthermore, a biasing member 426 (e.g., a coil spring) may be provided in the passageway 424 at a proximal end thereof. The biasing member 426 may be provided between the end cap 34 and the proximal end 418 of the displacement sensing arm 412. In this regard, the biasing member 426 may act on the proximal end 418 of the displacement sensing arm 412 to bias the displacement sensing arm 412 distally relative to the passage 424 and drill housing 26.

As such, the displacement sensing arm 412 may include features that selectively prevent ejection of the displacement sensing arm 412 from the distal end of the passage 424. For example, the displacement sensing arm 412 may include at least one flat 428 that extends along a portion of the arm 412. At the proximal and distal extents of the flat 428, the displacement sensing arm 412 may include shoulders 436 that project from the flats 428 (best seen at the distal portion 414 in FIG. 10B and at the proximal portion 418 in FIG. 11). As such, at the proximal opening of the passage 424, a selectively displaceable stop 438 (best seen in FIG. 23) may be disposed relative to the flat 428 such that the flat 428 may move relative to the stop 438, but interfere with the shoulder 436 defined in the displacement sensing arm 412 to prevent passage of the shoulder 436 beyond the stop 438. In this regard, the length of the displacement sensing arm 412 along which the flat 428 extends may be moveable relative to the stop 438, and the stop 438 may limit proximal and distal movement of the displacement sensing arm 412 beyond the stop 438.

However, the stop 438 may be displaceable upon depressing, for example, a button 440 provided on an exterior of the housing 26. Thus, upon depressing the button 440, the stop 438 may be displaced away from the displacement sensing arm 412 to allow the shoulder 436 to pass distally from the distal end of the passage 424 such that the displacement sensing arm 412 may be removed entirely from the passage 424. The distal end of the flats 438 may include a detent 442 that may be engageable with the stop 438 so as to maintain the displacement sensing arm 412 in a proximally disposed, retracted position relative to the housing (e.g., as shown in FIG. 11). Once the button 440 is depressed and released, the detent 442 at the proximal end of the flat 428 of the displacement sensing arm 412 may be released by the stop 438 and the displacement sensing arm 412 may move proximally (e.g., under influence of the biasing member 426). The displacement sensing arm 412 may move proximally until the shoulder 436 at the distal end of the flat 428 are engaged to prevent further distal movement of the displacement sensing arm 412. Accordingly, the displacement sensing arm 412 may be retained in a retracted position (e.g., for improved visibility of the distal end of the drill bit 16), released to be moveable relative to and biased proximally with respect to the housing 26, and removable altogether from the housing 26.

In the latter regard, removal of the displacement sensing arm 412 and biasing member 426 from the passage 424 may allow for separate cleaning (e.g., in an autoclave) of those members. Additionally, removal of the end cap 34 may allow for a cleaning apparatus (e.g., a brush or the like) to be passed through the full length of the passage 424 to facilitate cleaning thereof.

As referenced above, the distal portion 414 of the displacement sensing arm 412 may be adapted to engage a drill bit assembly 60 (e.g., a bushing 452 thereof) that is correspondingly adapted for use with the drill 50. For instance, as shown in FIGS. 10A-10C and FIG. 11, the displacement sensing arm 412 may generally be linear along the proximal portion 418 of the displacement sensing arm 412. In this regard, the proximal portion 418 may be adapted to be collinear with the passage 424 and moveable within the passage 424. Furthermore, the distal portion 414 of the displacement sensing arm 412 (e.g., the portion distal to the linear portion of the displacement sensing arm 412) may extend from the linear portion of the displacement sensing arm 412 toward the drill bit assembly 60 that may be engaged by the chuck 420 of the drill 50. In this regard, the linear portion of the displacement sensing arm 412 may be substantially parallel to and offset from the axis of rotation 120. The distal portion 414 may extend from the linear portion in a direction corresponding with the offset such that the distal portion 414 extends toward the drill bit assembly 60. This may facilitate engagement between the displacement sensing arm 412 and the bushing 454 of the drill bit assembly 60. As shown, in FIGS. 10A-10C and 11, the distal portion 414 may be an at least partially arcuate member extending along a radius of curvature toward the drill bit assembly 60. However, the distal portion 414 may be shaped differently (e.g., the distal portion 414 may be a linear portion extending at an angle or perpendicularly from the proximal 418 toward the drill bit assembly 60).

Figure 12:
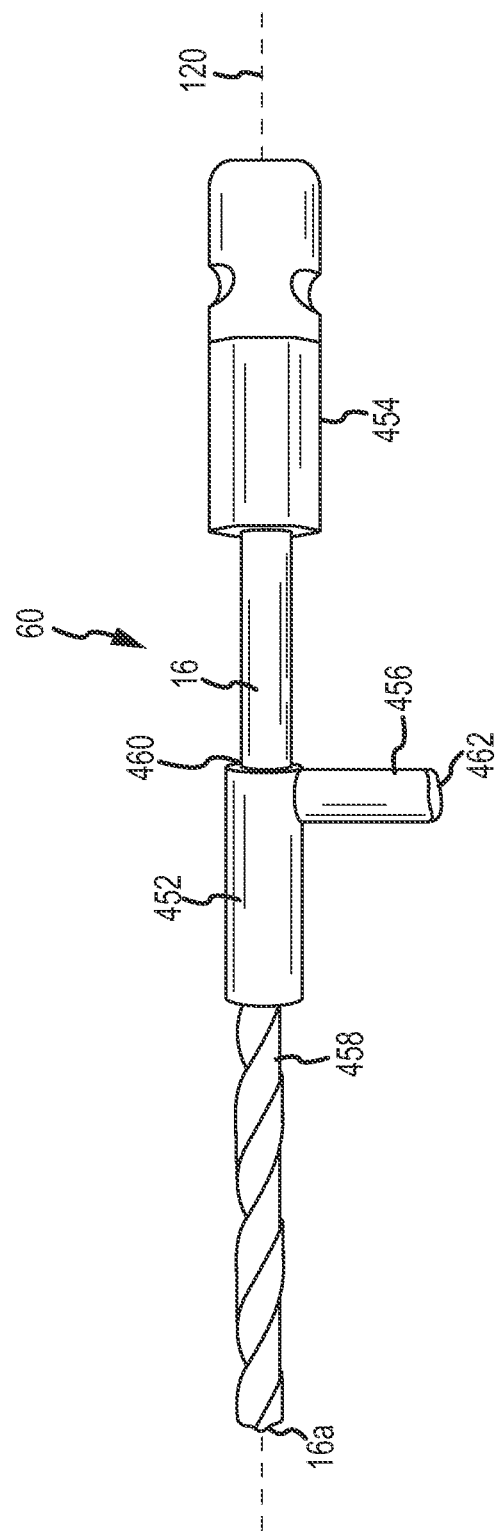
FIG. 12 is a side view of a drill bit assembly for use with an embodiment of a drill comprising a drill bit penetration measurement system.

With further reference to FIG. 12, an embodiment of a drill bit assembly 60 that may be used in conjunction with the drill 50 is depicted. The drill bit assembly 60 may include a shank 454 that is disposed adjacent to a proximal end of the assembly 60. Furthermore, the assembly 60 may comprise a leading edge 16a at the distal end thereof. The leading edge 456 may include a cutting edge that, when rotated serves to cut the medium into which the bit 16 is advanced as per a standard drill bit. A cylindrical member 458 (e.g., at least a portion thereof having flutes provided therein to remove cut material from the cutting edge) may extend between the shank 454 and the leading edge 456. The leading edge 456, cylindrical body 458, and shank 454 may collectively define the drill bit 16.

In addition to the drill bit 16, the drill bit assembly 60 may also comprise a bushing 452 as referenced above. The bushing 452 may engage the cylindrical member 458 to facilitate relative movement of the bushing 452 relative to the cylindrical member 458 along a direction corresponding to the axis of rotation 120. For example, the bushing 452 may include an aperture 460 through which at least a portion of the cylindrical member 458 may be disposed. The aperture 460 may form a cylindrical opening that extends at least in a direction corresponding to the axis of rotation 120 of the drill bit 16. The cylindrical opening may be sized to receive the cylindrical member 458 therein such relative movement between the cylindrical opening and the cylindrical member 458 is provided. As such, the drill bit 16 may be free to rotate within the aperture 460, and the bushing 452 may slideably engage the cylindrical member 458 for relative movement therebetween that is constrained along the direction corresponding to the axis of rotation 120.

The bushing 452 may include an engagement member 456 that is disposed on the bushing 452 and adapted for engagement with a displacement sensing arm 412 of a drill 50 to which the drill bit assembly 60 is engaged. For instance, as depicted in FIG. 12, the engagement member 456 may comprise a post 462 extending from the bushing 452. The post 462 may extend away from the axis of rotation 120 of the drill bit assembly 60. In an embodiment, the post 462 may extend perpendicularly to the axis of rotation 120. Accordingly, the post 462 may engage a hole 464 provided on the distal portion 414 of the displacement sensing arm 412. In this regard, the post 462 may extend into the hole 464. Movement of the bushing 452 relative to the drill bit 16 in a direction corresponding to the axis of rotation 120 may result in the post 462 acting on the hole 464 such that the displacement sensing arm 412 undergoes corresponding movement upon movement of the bushing 452 relative to the drill bit 16. In turn, as described above, the core 422 at the proximal portion 418 the displacement sensing arm 412 may also undergo corresponding movement relative to the coil 416, which may be detected by the displacement sensor 410 and output as a displacement measure.

It may be appreciated that other arrangements for engaging the bushing 452 with the displacement sensing arm 412 may be provided so that the bushing 452 and displacement sending arm 412 undergo corresponding movement. For example, other structures such as clasps, fasteners, or other mechanisms may be utilized to engage the bushing 452 to the displacement sensing arm 412. Furthermore, the bushing 452 may, in some embodiments, be integrally defined on the distal portion 414 of the displacement sensing arm 412. In this regard, a standard drill bit 16 may be engaged with a chuck 420 of the drill 50 and the bushing 452 may be disposed relative to the bit 16. In any regard, the bushing 452 may be pivotal relative to the displacement sensing arm 412 (e.g., in a direction perpendicular to the axis of rotation 120) to facilitate ease of engagement of the bushing 452 with the displacement sensing arm 412 or the bushing 452 with the drill bit 16 when engaging the drill bit 16 with the chuck 420 of the drill 50.

Figure 20A:
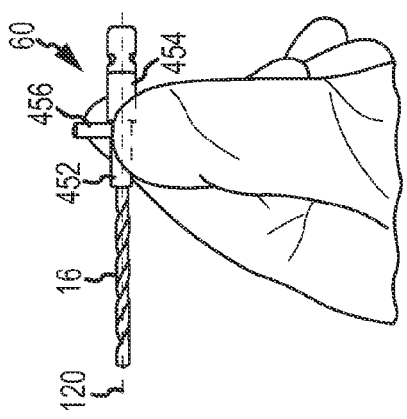
FIGS. 20A-20D depict a progression for engagement of a drill bit assembly with a drill having a drill bit penetration measurement system.
Figure 20B:
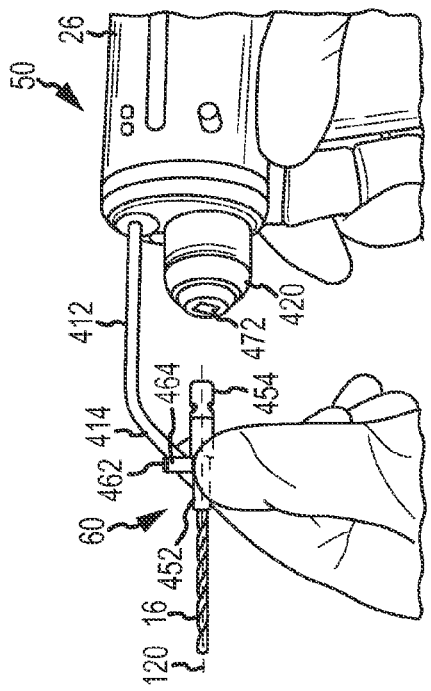
Figure 20C:
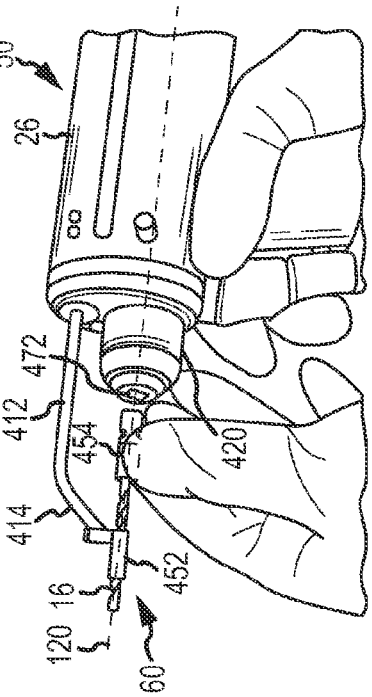
Figure 20D:
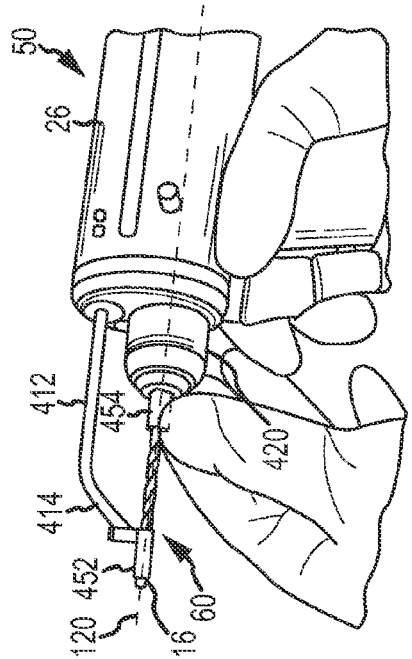

For example, with reference to FIGS. 20A-20D, a progression of images are shown that illustrate engagement of the drill bit assembly 60 with a drill 50. In FIG. 20A, the drill bit assembly 60 is grasped by a user at the bushing 452. Thereafter in FIG. 20B, the post 462 of the bushing 452 is disposed in a hole 464 of the displacement sensing arm 412 extending from the drill housing 26. As may be appreciated, given the cylindrical interface between the post 462 and the hole 464, the bushing 452 and drill bit 16 may still be rotatable perpendicularly to the axis of rotation 120. As such, the shank 454 may be aligned with the chuck 420 as shown in FIG. 20C. Thereafter, the drill bit 16 may be moved proximally such that the chuck 420 engages the shank 454. As shown and described in greater detail below, the chuck 420 may comprise a "quick-change" style chuck that allows for rapid insertion and removal of drill bits 16 therefrom. However, other types of chucks may be utilized without limitation such as, for example, a jawed chuck, a collet, a magnetic chuck, etc.

In any regard, the shank 454 of the drill bit assembly 60 may be engaged with the chuck 420 of the drill 50. In this regard, the drill bit 16 may be fixed relative to the drill 50 in the direction along the axis of rotation 120. In turn, the bushing 452 may be displaceable relative to the drill bit 16 along the axis of rotation 120. In this regard, when the drill bit 16 is advanced into a medium during a drilling operation, the bushing 452 may remain stationary at a reference point established prior to the drilling operation and the displacement sensor 410 may be operable to detect the relative motion between the drill bit 16 and the bushing 452 retained in a stationary position relative to the reference point, thus providing a measure of the relative movement of the drill bit 16 relative to the reference point.

Figure 22:
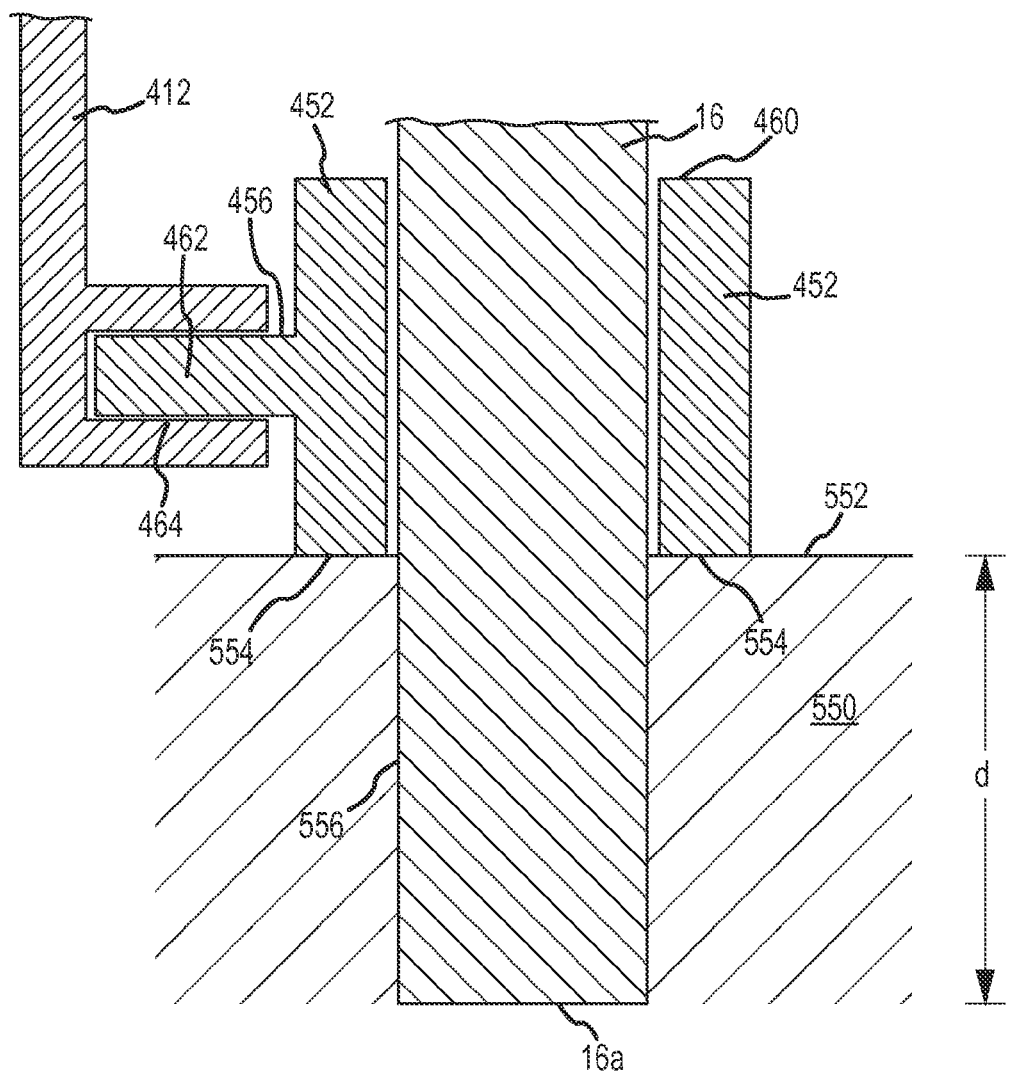
FIG. 22 is a cross sectional schematic view of a drill bit that has been advanced into a bore in a medium relative to a bushing engaged with a distal portion of a displacement sensing arm.

For instance, with further reference to FIG. 22, a schematic section view of a drill bit 16 that has been advanced into a medium 550 is shown. The bushing 452 may be disposed about the drill bit 16. As such, the bushing 452 may be disposed about the periphery of the bore 556 created upon advancement of the drill bit 16 into the medium 550. That is, the bushing 452 may remain in contact with the surface 552 of the medium 550 upon advancement of the drill bit 16 into the medium 550. In this regard, the bushing 454 may include a reference surface 554 at a distal portion thereof. The reference surface 554 may contact the surface 552 of the medium 550 to be drilled. As such, prior to initiation of the drilling when the leading edge 16a of the drill bit 16 is also in contact with the surface 552, the displacement sensor 410 may be set to establish the reference point. Accordingly, as the drill bit 16 is advanced, the reference surface 554 may remain in contact with the surface 552 of the medium 550. The reference surface 554 may contact the surface 552 about a periphery of the bore 556. In an embodiment, the reference surface 554 may extend circumferentially about a majority or substantially all of the drill bit 16 such that the reference surface 554 may also extend circumferentially about a majority of or substantially all of the periphery of the bore 556. The distally biased displacement sensing arm 412 may act on the bushing 452 (e.g., by way of post 462 received in hole 464) to maintain the bushing 452 in contact with the surface 552. In any regard, the displacement (d) of the leading edge 16a of the drill bit 16 relative to the reference surface 554 of the bushing 454 may be measured upon corresponding movement of the core 422 at the proximal end 418 of the displacement sensing arm 412 relative to the coil 416.

In this regard, measurement of the displacement of the leading edge 16a of the drill bit 16 relative to the reference surface 554 of the bushing 454 that is maintained against the surface 552 of the medium 550 to be drilled may provide improved accuracy regarding the displacement of the leading edge 16a into the bore 556. As described above, as the reference surface 554 is maintained in contact with the medium 550 adjacent to the periphery of the bore 556, there is less possibility for relative movement between the bushing 452 and the medium 550 that may introduce error into the measured displacement d. Furthermore, as the bushing 452 is in contact with the medium 550 adjacent to the bore 556, the contact with the patient required to obtain the measurement is lessened as the extension 110 may not need to contact the patient in a location away from the bore 556. Thus, the drilling operation is less invasive, thus improving patient outcomes.

A number of additional features may also be provided for the drill 50 and/or drill bit assembly 60 that are described in conjunction with the embodiment of the drill 50. It may be appreciated that these features may be provided with other types of drills and/or drill bit assemblies 60 and are not required to be used in conjunction with a drill 50 and drill bit assembly 60 incorporating features for coordinated operation between the displacement sensor 410 and drill bit assembly 60 as described above.

Figure 13:
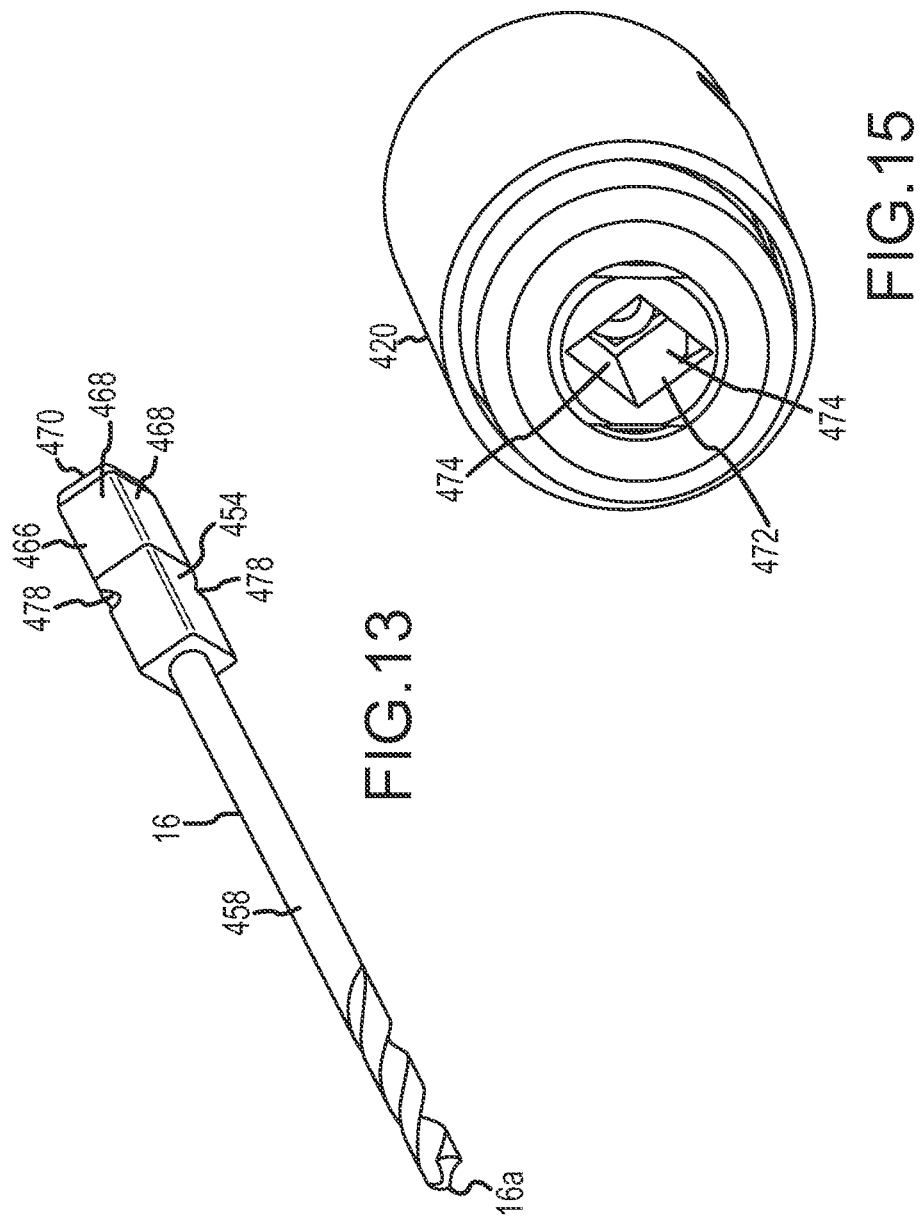
FIG. 13 is a perspective view of an embodiment of a drill bit with an intact destructible portion.
Figure 14:
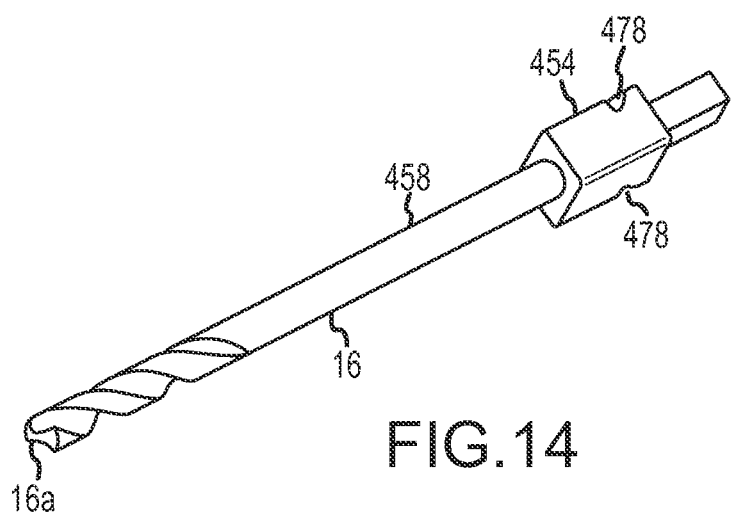
FIG. 14 is a perspective view of the embodiment of the drill bit of FIG. 13, wherein the destructible portion has been at least partially destroyed.

For instance, as may be further appreciated with reference to FIGS. 13-15, a drill bit 16 may incorporate features that prevent reuse of the drill bit 16. In this regard, surgical drill bits are often employed as single use items such that the bits are specifically designed to be used for a single procedure or portion thereof and disposed after use rather than being reused. There are several rationales for doing so, including the safety of the patient to ensure that the drill bit 16 to be used in a procedure has not been worn or damaged by use in previous procedures. In this regard, the features described below may help prevent the drill bit 16 from being reused. As may be appreciated, the drill bit 16 disclosed in this respect may be used in a drill bit assembly 60 as described above.

Specifically, the drill bit 16 may include a destructible portion 466 of the shank 454. The destructible portion 466 may be degraded or destroyed when exposed to common cleaning procedures to which surgical instruments are routinely exposed. Upon destruction of the destructible portion 466, the shape of the shank 454 may be altered. The altered shape of the shank 454 may result in a reduced ability to engage the drill bit 16 with a chuck 420. Such cleaning procedures may include exposure to steam cleaning at elevated heat and/or pressure in an autoclave process or may include exposure to cleaning chemicals or the like. In this regard, when, for example, the destructible portion 466 is exposed to temperatures associated with cleaning in an autoclave, the destructible portion 466 may be degraded or destroyed (e.g., by melting or other degradation due to heat) to prevent reuse of the drill bit assembly 60. Accordingly, in an embodiment, the melting temperature of the destructible portion may be greater than an operating temperature (e.g., substantially similar to room temperature or 22.3° C.+/−20° C.). Accordingly, in an embodiment, the melting temperature may be not less than about 50° C. and not greater than about 130° C. In an embodiment, the melting temperature of the destructible portion may be not less than about 60° C. and not greater than about 110° C.

While autoclave cleaning is a common method of sterilization and cleaning of instruments between procedures, it may be appreciated that other methods of cleaning may be employed. As such, the destructible portion 466 may be adapted to be degraded or destroyed during such cleaning procedures. For example, the destructible portion 466 could alternatively or additional be adapted to be degraded or destroyed upon exposure to a cleaning element such as a cleaning chemical or the like. In any regard, upon an attempt to sterilize or otherwise clean the drill bit assembly 60 for reuse, the destructible portion 466 may be destroyed or degraded to the point of eliminating the effectiveness of the drill bit assembly 60 to prevent reuse of the drill bit assembly 60.

With further reference to FIG. 13, one particular embodiment of a drill bit assembly 60 including a destructible portion 466 is shown where the destructible portion may comprise a portion of the shank 454 of the drill bit assembly 60. As shown, the destructible portion 466 comprises a proximal end of the shank 454. As such, at least a portion of a sidewall 468 and/or an endwall 470 of the shank may be defined by the destructible portion 466. As may be appreciated with further reference to FIGS. 15 and 16, the shank sidewall 468 and endwall 470 may be adapted for engagement with the chuck 420 such that the chuck 420 contacts the sidewalls 468 and endwall 470 upon engagement with the shank 454.

For instance, as shown in FIG. 15, the chuck 454 may include a correspondingly-shaped opening 472 that is sized to have corresponding sidewalls 474 that may contact the sidewalls 468 of the shank 454 when the shank 454 is received in the chuck opening 472. For instance, as shown, the sidewall 468 of the shank 454 may generally be arranged in a square and the chuck sidewall 474 of the chuck opening 472 may be correspondingly shaped and sized to accommodate the sidewalls 468. As such, upon receipt of the shank 454 in the chuck opening 472, the chuck sidewalls 474 and shank sidewalls 468 may define a bearing surface interface that allows the chuck 420 to impart rotational motion to the drill bit 16. Furthermore, the chuck opening 472 may have a depth that allows the endwall 470 of the shank 454 to register relative to the chuck opening 472 when the shank 454 is received in the chuck opening 472.

Accordingly, when, as shown in FIG. 14, the destructible portion 466 is destroyed or degraded, at least a portion of the sidewall 468 or endwall 470 may be removed. The result may be at least a lack of registration of the shank 454 relative to the chuck opening 472. This may prohibit the ability of the drill bit assembly 60 to be used because the lack of registration may prevent the drill bit 16 from properly turning so as to at least inhibit the use of the drill bit assembly 60 in a procedure. For instance, the bearing surface interface between the chuck sidewalls 474 and the shank sidewall 468 may be degraded such that the chuck 420 may not be capable of imparting rotational motion to the drill bit 16. Additionally or alternatively, the destructible portion 466 may be degraded to the point where the shank 454 is no longer receivable by the chuck 420.

As may also be appreciated in FIGS. 13 and 14, the shank 454 may include chuck engagement features that may be engaged by the chuck 420 to retain the drill bit assembly 60 relative to the chuck 420. For instance, the chuck 420 may include retention pins 476 that are biased to extend into the chuck opening 472 from the chuck sidewall 474 in an engaged position to engage detents 478 of the shank 454. For instance, a biasing member 480 may bias a chuck collar 482 distally relative to the chuck opening 472. The collar 482 may be engaged with the pins 476 to bias the pins 476 into the engaged position. Upon movement of the collar 482 proximally relative to the chuck opening 472, the pins 476 may be freed so as to allow movement away from the engaged position (e.g., to receive the shank 454 or release the shank 454 during normal operation as is common with "quick-release" type chucks). Correspondingly, the detents 478 of the shank 454 may be released and the shank 454 may be released from the chuck 454. In an embodiment, the destructible portion 466 may include the detents 478 such that the shank 454 may not be retained by the pins 476 once the destructible portion 466 is degraded or destroyed.

Figure 17:
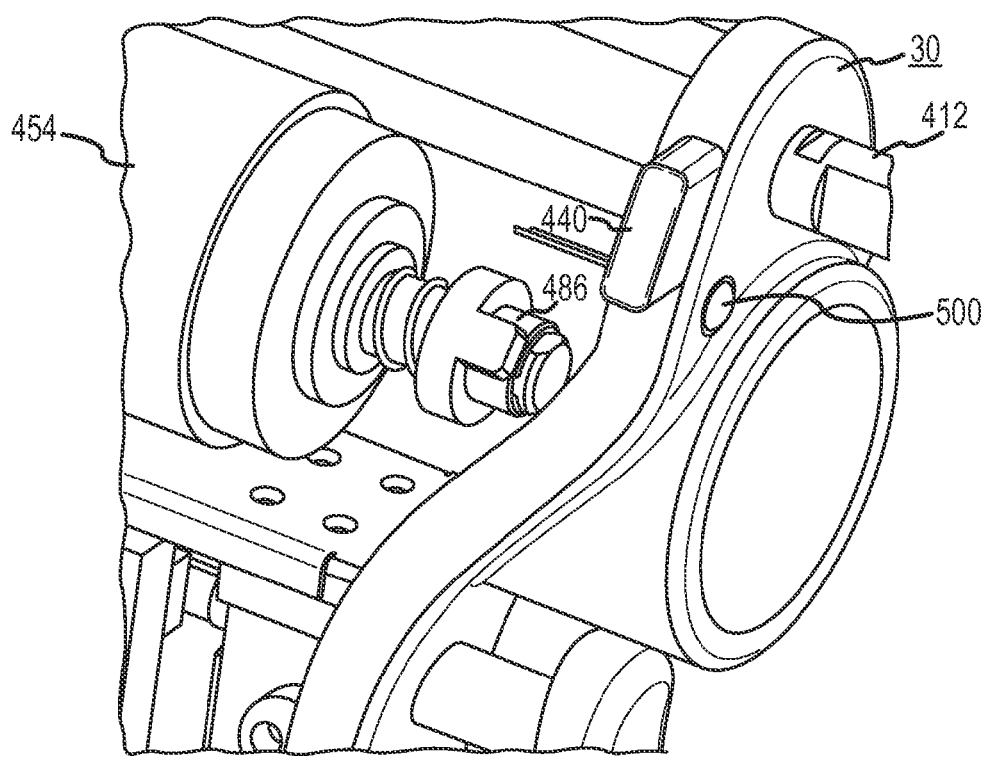
FIG. 17 is a perspective view with a portion of the drill housing cut away to show an embodiment of a coupling of a drill that corresponds to the chuck of FIG. 15.

Furthermore, the drill 50 may include a removable chuck 420 that provides for quick interchange and/or removal of the chuck 420. As may further be appreciated from FIG. 11, the drill 50 may include a drive 430. The drive 430 may a motor 432 and gearbox 434. The drive 430 may engage a chuck 420. Specifically, the chuck 420 may be provided in removable engagement with the drive 430 such that the chuck 420 may be releasably engaged with the drive 420. As may be further appreciated in FIG. 16, the chuck 454 may include a chuck drive coupling 484 at a proximal end thereof. In this regard, as may be appreciated in FIG. 17, the drill 50 may include a corresponding drill drive coupling 486 that engages with the chuck drive coupling 484 to impart rotational motion from the drive 430 to the chuck 420. In this regard, the chuck 420 may be detachable from the drill 50.

Figure 18:
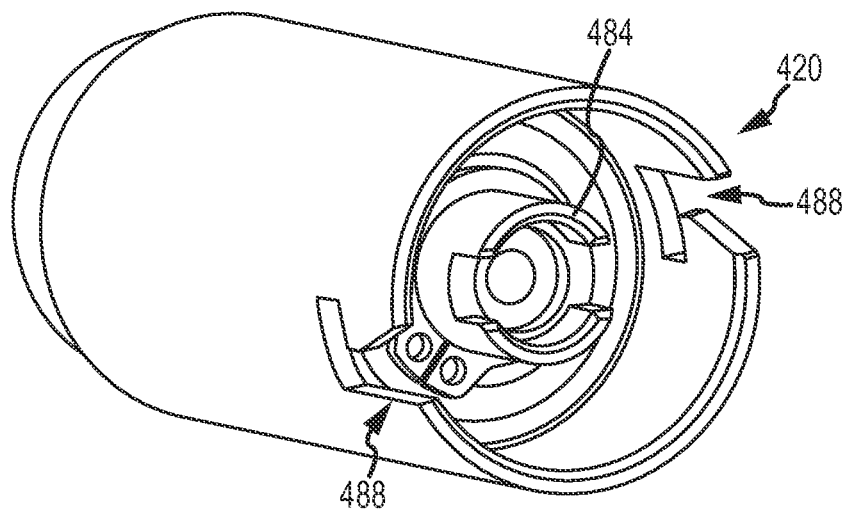
FIG. 18 is a perspective view of the proximal end of the chuck of FIG. 15.

For instance, with further reference to FIG. 18, the proximal end of the chuck 420 may include slots 488 that may coordinate with corresponding tabs 490 (best seen in FIG. 19B) to retain the chuck 420 relative to the drill 50 such that the dill drive coupling 486 engages the chuck drive coupling 484 to impart rotational motion thereto. The slots 488 may coordinate with the tabs 490 so to allow the chuck 420 to be quickly attached and/or released from the drill 50 by engagement of the slots 488 with the tabs 490. The tabs 490 may be operatively engaged with a release 492. Accordingly, upon actuation of the release (e.g., from the exterior of the drill housing 26), the tabs 490 may disengage the chuck 420 to allow the chuck to be removed. Thus, the chuck 420 may be quickly and efficiently attached and detached from the drill 50.

With further reference to FIGS. 19A and 19B, cross sectional views of the drill 50 with drill bit assembly 60 engaged therewith are shown. As may be appreciated, the drill drive coupling 486 may engage the chuck drive coupling 484. As may also be appreciated, the chuck 450 may be operatively engaged with the drill drive 430 such that the engagement of the slots 488 of the chuck 420 are engaged with the tabs 490 disposed relative to the drill body 26. As may also be appreciated in FIGS. 19A and 19B, a destructible portion 466 of the shank 454 may be intact such that the sidewalls 468 the shank 454 are in registration with corresponding sidewalls 470 of the chuck opening 472 and the endwall 470 of the shank 454 is seated against the proximal end of the chuck opening 472. Furthermore, the detents 478 in the shank 454 may coordinate with the pins 476 that are biased relative to the detents 476 by way of the action of the distally biased collar 482 thereon. In this regard, the drill bit 16, chuck 420, and drill drive 430 may comprise a rigid assembly along a direction corresponding to the axis of rotation 120. Accordingly, as will be described in greater detail below, a force acting on the leading edge 16a of the drill bit 16 may in turn be transmitted throughout the rigid assembly.

With specific reference to FIG. 19A, it may be appreciated that the bushing 452 of the drill bit assembly 60 may be engaged with the distal portion 414 of the displacement sensing arm 412. Accordingly, as may be appreciated, the drill bit 16 may be operatively engaged with the chuck 420 so as to limit relative movement therebetween along the axis of rotation 120 such that relative movement between the bushing 452 and displacement sensing arm 412 may be sensed as described above.

As may be appreciated, when drilling using the drill 50, a second sensor for measurement of force acting on the leading edge 16a of the drill bit 16 may also be provided. In this regard, a second sensor 118' (e.g., a force sensor such as piezoelectric crystal) may be disposed proximally to the drill drive 430. In turn, force acting on the leading edge 16a of the drill bit 16 as it is advanced in the drilling process may be transferred to the second sensor 118' via the drill drive 430. That is, the force acting on the leading edge 16a of the drill bit 16 may be transferred through the shank 454 of the bit 16 to the chuck 420, and the drill drive 420. In turn, the drive 430 may act upon the second sensor 118' to produce an output corresponding to the force acting on the leading edge 16a. In this regard, it may be appreciated that the rigid assembly of the drill drive 430, chuck 420, and drill bit 16 may transmit the force acting on the leading edge 16a of the drill bit 16 to the second sensor 118. It may further be appreciated that the drill drive 430 may be fixed rotationally relative to the drill housing 26 so as to impart rotation to the chuck 420. However, the drill drive 430 is preferably free to move in a direction along the axis of rotation 120 such that the at least a majority of the force acting on the leading edge 16a of the drill bit 16 may be transferred to the second sensor 118. In an embodiment, the second sensor 118 may have a range of measureable force from about 0 lbf (0 N) to about 100 lbf (445 N). In an embodiment, the second sensor 118 may have a range of measurable force from about 0 lbf (0 N) to about 25 lbf (111 N). The second sensor 118 may have a precision of at least about 1% of the maximum measureable force. Accordingly, in an embodiment, the second sensor may have a precision of at least about 0.25 lbf (1.1 N). In an embodiment, the second sensor 118 may have a precision of 0.5% (e.g., about 0.125 lbf (0.56 N) in an embodiment).

In this regard, the drill drive 430, as shown best in FIGS. 11 and 19A may be mounted to the drill housing 26 by way of a suspension member 494. The suspension member 494 may be operatively engaged to the drill housing 26 and the drill drive 430 so as to maintain the drill drive 430 stationary with respect to rotation about to the axis of rotation 430, yet allow for at least some movement of the drill drive 430 axially relative to the axis of rotation 120 to transfer force acting on the leading edge 16a of the drill bit 16 to the second sensor 118. As such, the suspension member 494 may be supportively engaged to the drill drive 430 at a first end of the suspension member 494. The suspension member 494 may also be affixed to the drill housing 26. The suspension member 494 may be relatively rigid relative to a direction corresponding to rotation about the axis of rotation 120 so as to maintain the drill drive 430 stationary with respect to rotation about the axis of rotation. However, the suspension member 494 may allow for linear movement along the axis of rotation 120. In this regard, the suspension member 494 may comprise a spring member that allows for motion relative to the direction along the axis of rotation 120. The spring member may have a spring coefficient slight enough relative to the direction corresponding to the axis of rotation 120 such that the force resulting from displacement of the suspension member 494 may be insignificant (e.g., less than about 1%, less than about 0.5% or even less than about 0.1%) of the force applied to the leading edge 16a of the drill bit 16 during the drilling operation. It may be appreciated that the drill drive 430 may additionally or alternatively mounted relative to the housing 26 to facilitate movement in the direction along the axis of rotation 120 while resisting rotational movement about the axis of rotation 120. For instance, the drill drive 430 may incorporate a tab 136 and slot 138 as described above relative to chuck 28 to facilitate linear motion along the axis of rotation 120 while resisting rotational motion about the axis of rotation 120.

The drill may also include a light emitter 500 disposed on a distal face 30 of the drill hosing 26. In this regard, the light emitter 500 may be operable to emit light in a direction toward the drill bit 16 when engaged with the chuck 420. As such, the light emitter 500 may illuminate at least a portion of the drill bit 16 during the drilling operation to improve visibility of the medium being drilled. The light emitter 500 may comprise a light source such as, for example, an incandescent bulb, a light emitting diode (LED), a laser source, or other light source known in the art. Alternatively, a light source may be disposed remotely from the light emitter 500 and the light may be transmitted from the remote light source to the light emitter 500 using optical elements such as fiber optics or the like. It may further be appreciated that a light emitter 500 like the one shown in the accompanying figures may be provided with other types of surgical instruments without limitations. For example, a light emitter 500 of the type described herein may be provided with other types of drills, saws, or other surgical tools. Accordingly, the light emitter 500 may be appropriately disposed relative to the surgical field so as to direct light from the light emitter 500 toward the interface of the surgical tool with the portion of the surgical field contacted by the surgical tool.

The light emitter 500 may be selectively operated or may be operated when the drill 50 is operated. In this regard, the light emitter 500 may be selectively toggle on and off or may include different levels of intensity. The selector for the light emitter 500 may be at the controller housing 146 (e.g., a selectable option on the display 152). The light emitter 500 may also be activated upon activation of the drill 50. Additionally, the operation of the light emitter 500 may be selectable between operation with the drill 500 and selective toggling of the light emitter 500.

Figure 24A:
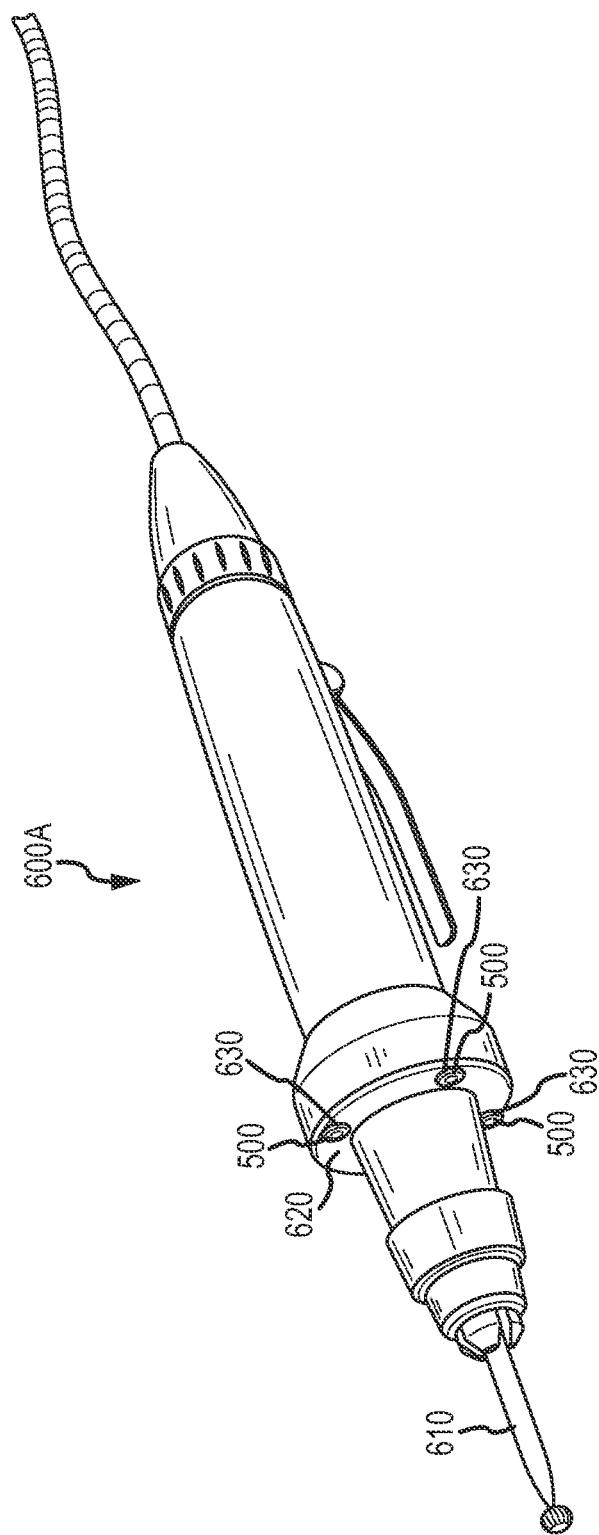
FIGS. 24A-24C depict various embodiments of surgical instruments including light emitters.
Figure 24B:
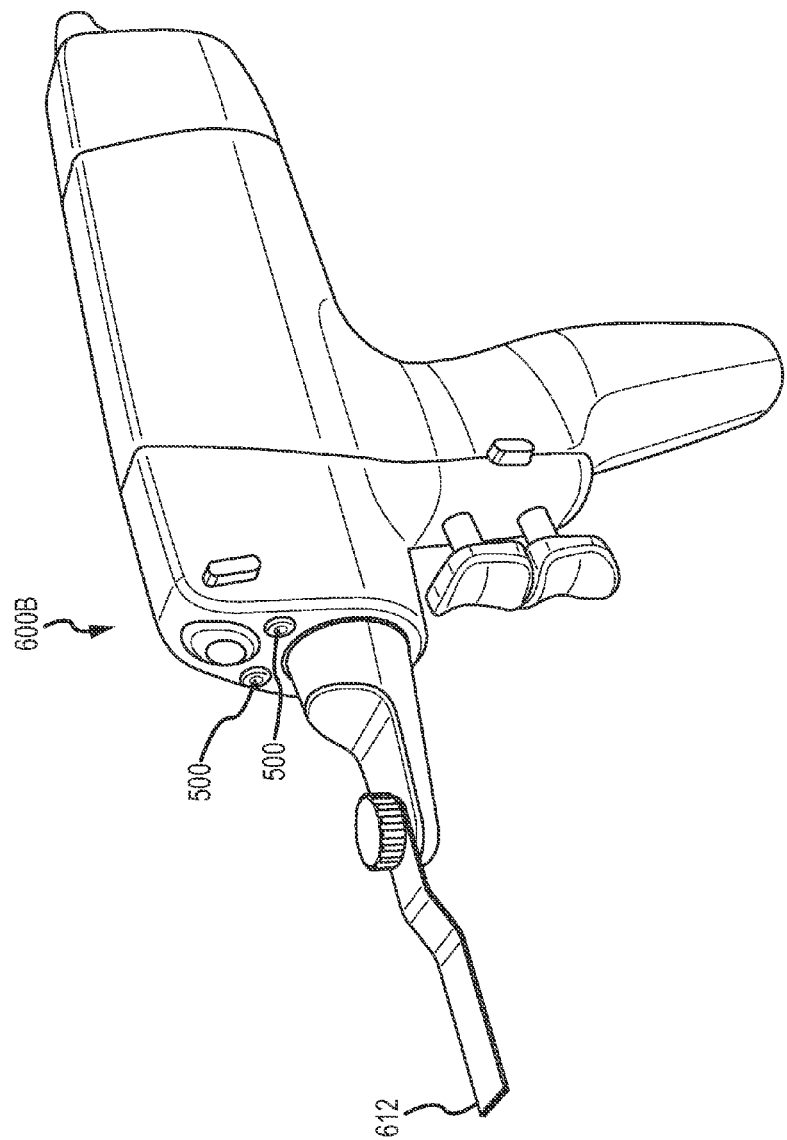
Figure 24C:
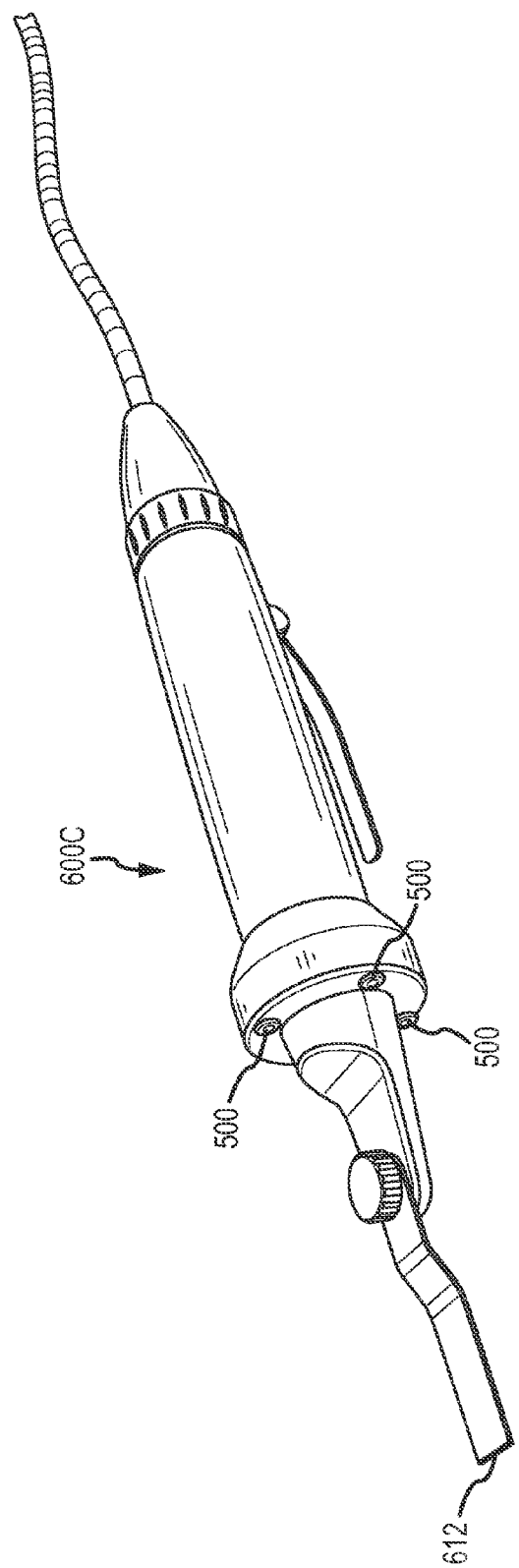

In a further embodiment, the light emitter 500 may be adapted for use with any appropriate surgical instrument. In this regard, further examples of surgical instruments are shown in FIGS. 24A, 24B, and 24C, respectively. For example, in FIG. 24A, a burr grinder 600A is shown, in FIG. 24B, a sagittal saw 600B is shown with a first grip embodiment, and in FIG. 24C, a sagittal saw 600C is shown with a second grip embodiment. In FIG. 24A, the burr grinder 600A may include an instrument working portion comprising a rotatable burr grinding bit 610. In this regard, the burr grinding bit 610 may be contactable with the patient to perform a grinding operation. The burr grinder 600A may also include one or more light emitters 500. As may be appreciated, the light emitters 500 may be disposed on a distal face 620 of the burr grinder 600A such that the light emitters 500 may be operable to emit light in a direction toward the patient when the burr grinding bit 610 is in contact with the patient. That is, the light emitter 500 may act to illuminate a surgical field in which the burr grinder 600A is employed. In the case of a plurality of light emitters 500, the light emitters may be spaced equally about a portion of the distal face 620 surrounding the working portion of the burr grinder 600A. The light emitters 500 may be disposed within a housing of the burr grinder 600A such that the light emitters 500 may be protected from environmental elements (e.g., fluid or the like) that may be present when the burr grinder 600A is in use. As such, the light emitters 500 may include or be disposed behind a transparent or translucent shield 630 that may protect the light emitters 500 and/or light source associated with the light emitters 500 from such environmental elements. The light emitters 500 shown in FIG. 24A may be operated according to any of the foregoing discussion regarding the light emitters 500 described above.

Furthermore, with further reference to FIGS. 24B and 24C, it may be appreciated that the light emitters 500 may be provided in connection with other surgical instruments. For instance, in FIG. 24B, a sagittal saw 600B with a first grip embodiment (i.e., a pistol grip style grip) is shown. In this regard, it may be appreciated that a sagittal saw blade 612 may be provided as the working portion of the sagittal saw 600B. As such, the sagittal saw blade 612 may be reciprocated such that contact of the distal portion of the sagittal saw blade 612 may act to cut anatomy of the patient. As such, the light emitters 500 may be disposed on a distal face of the sagittal saw 600B such that the light emitters 500 may emit light toward the patient when the sagittal saw blade 612 contacts the patient in a cutting operation. Further still, FIG. 24C shows another embodiment of a sagittal saw 600C with a second grip embodiment. As may be appreciated, the light emitters 500 of the sagittal saw 600C may be disposed about the sagittal saw blade 612 in a manner as described above with respect to the burr grinder 600A.

Those skilled in the art will appreciate that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A surgical instrument, comprising:
   a surgical instrument housing;
   an instrument working portion adapted to engage a portion of a patient to perform a surgical operation, wherein the instrument working portion extends along a first axis extending from the surgical instrument housing;
   a measurement system for determining, with respect to a reference point, a depth of the instrument working portion during the surgical operation;
   a first sensor of the measurement system that is disposed internally to the surgical instrument housing for outputting a first signal representative of a displacement, with respect to the reference point, of the instrument working portion, wherein the first sensor comprises a displacement sensing arm having a first portion extending from a passage extending through the surgical instrument housing along a second axis parallel to the first axis, and a second portion extending from the first portion toward the instrument working portion in a plane intersecting the first axis and the second axis, wherein the second portion is adapted for releasable engagement with a bushing member that is constrainedly movable relative to the instrument working portion along the first axis; and
   a light emitter disposed on a distal face of the surgical instrument housing adapted to emit light in a direction toward the patient when the instrument working portion is engaged with the portion of the patient to perform the surgical operation, wherein the light emitter is offset from the plane intersecting the first axis and the second axis.

2. The surgical instrument of claim 1, wherein the instrument working portion comprises at least one of a surgical drill, a surgical saw, or a surgical grinder.

3. The surgical instrument of claim 1, wherein the light emitter comprises a light emitting diode light source.

4. The surgical instrument of claim 3, wherein the light source is disposed within a housing of the surgical instrument.

5. The surgical instrument of claim 1, wherein the measurement system is for determining, with respect to a reference point, a depth of the instrument working portion when the instrument working portion passes from a first medium to a second medium, the first medium contiguous with the second medium, the first medium having a first density, the second medium having a second density, the measurement system further comprising:
   a second sensor outputting a second signal representative of a force applied to the instrument working portion;
   a processor in electrical communication with the first and second sensors, the processor configured in a first mode to output a third signal representative of the depth of penetration of the instrument working portion of the surgical instrument when the instrument working portion passes from the first medium to the second medium, the third signal based on the first and second signals.

6. The surgical instrument of claim 1, wherein the light emitter is selectively operable between an emitting state and a non-emitting state.

7. The surgical instrument of claim 6, wherein the emitting state occurs upon operation of the instrument working portion, and the non-emitting state occurs upon cessation of operation of the instrument working portion.

* * * * *